(12) United States Patent
Broglie et al.

(10) Patent No.: US 7,109,392 B1
(45) Date of Patent: Sep. 19, 2006

(54) METHODS FOR INCREASING OLEIC ACID CONTENT IN SEEDS FROM TRANSGENIC PLANTS CONTAINING A MUTANT DELTA 12 DESATURASE

(75) Inventors: Richard Martin Broglie, Landenberg, PA (US); Lorin Roger DeBonte, Ft. Collins, CO (US); William Dean Hitz, Wilmington, DE (US); Guo-Hua Miao, Hockessin, DE (US); Robert Stefan Reiter, Urbandale, IA (US)

(73) Assignee: Cargill, Incorporated, Minneapolis, MN (US)

( * ) Notice: Subject to any disclaimer, the term of this patent is extended or adjusted under 35 U.S.C. 154(b) by 0 days.

(21) Appl. No.: 09/643,579

(22) Filed: Aug. 22, 2000

Related U.S. Application Data

(63) Continuation of application No. 09/232,948, filed on Jan. 19, 1999, now abandoned, which is a continuation of application No. 08/728,025, filed on Oct. 9, 1996, now abandoned.

(51) Int. Cl.
*C12N 15/05* (2006.01)
*C12N 15/29* (2006.01)
*C12N 15/82* (2006.01)

(52) U.S. Cl. .................. 800/281; 800/287; 800/298; 800/306; 800/312; 800/314; 800/320.1; 435/320.1; 536/23.1; 536/23.2; 536/23.6

(58) Field of Classification Search ............... 800/278, 800/281, 295, 298, 306, 287, 312, 314, 320.1; 435/183, 320.1; 536/23.1, 23.2, 23.6
See application file for complete search history.

(56) References Cited

U.S. PATENT DOCUMENTS

| | | | |
|---|---|---|---|
| 5,638,637 A | 6/1997 | Wong et al. | 47/58 |
| 5,668,299 A | 9/1997 | Debonte et al. | 800/230 |
| 5,850,026 A | 12/1998 | DeBonte et al. | |
| 6,063,947 A | 5/2000 | DeBonte et al. | |
| 6,372,965 B1 * | 4/2002 | Lightner et al. | 800/298 |

FOREIGN PATENT DOCUMENTS

| | | |
|---|---|---|
| CA | 2180386 | 1/1998 |
| WO | 93/11245 | 6/1993 |
| WO | WO 93/11245 | 6/1993 |
| WO | 94/11516 | 5/1994 |
| WO | WO 94/11516 | 5/1994 |
| WO | WO 94/18337 | 8/1994 |
| WO | WO 96/06936 | 3/1996 |
| WO | WO 96/21022 | 7/1996 |
| WO | WO 97/21340 | 6/1997 |
| WO | WO 97/30582 | 8/1997 |
| WO | WO 97/47731 | 12/1997 |

OTHER PUBLICATIONS

U.S. Appl. No. 08/572,027, filed Dec. 1995, L. DeBonte.*
Kallis R. et al., Plant Physiology, Jul. 2000, vol. 123, pp. 1077-1086.*
Osawa S. et al. Journal of Biological Chemistry, Mar. 15, 1991; vol. 266, No. 8, pp. 4673-4676.*
Okuley et al., *The Plant Cell*, 6, 147-158, Jan. 1994.
Shanklin et al., *Biochemistry*, 33, 12787-12794, 1994.
Topfer et al., *Science*, 268, 681-686, May 1995.
Broun et al., *The Plant Journal*, 13(2), 201-210, 1998.
Rakow, "Selection for Linoleic and Linolenic Acid Content in Rape Seed after Mutagenic Treatment," Z. Pflanzenzüchtg, 69:62-82 (1973).
Avelange-Macherel et al., "Site-directed mutagenesis of histidine residues in the delta 12 acyl-lipid desaturase of Synechocystis," *FEBS Lett.*, 1995, 361:111-114.

* cited by examiner

*Primary Examiner*—Russell P. Kallis
(74) *Attorney, Agent, or Firm*—Fish & Richardson P.C.

(57) ABSTRACT

The preparation and use of nucleic acid fragments encoding fatty acid desaturase enzymes are described. The invention permits alteration of plant lipid composition. Chimeric genes incorporating mutant delta-12 fatty acid desaturase nucleic acid fragments with suitable regulatory sequences may be used to create transgenic plants with altered levels of unsaturated fatty acids.

15 Claims, 4 Drawing Sheets

METHODS FOR INCREASING OLEIC ACID CONTENT IN SEEDS FROM TRANSGENIC PLANTS CONTAINING A MUTANT DELTA 12 DESATURASE

This is a continuation of application Ser. No. 09/232,948 filed Jan. 19, 1999, now abandoned which is a continuation of application Ser. No. 08/728,025 filed Oct. 9, 1996, now abandoned.

FIELD OF THE INVENTION

The invention relates to the preparation and use of nucleic acid fragments encoding fatty acid desaturase enzymes to modify plant lipid composition. Chimeric genes incorporating such nucleic acid fragments and suitable regulatory sequences may be used to create transgenic plants with altered levels of unsaturated fatty acids.

BACKGROUND OF THE INVENTION

Plant lipids have a variety of industrial and nutritional uses and are central to plant membrane function and climatic adaptation. These lipids represent a vast array of chemical structures, and these structures determine the physiological and industrial properties of the lipid. Many of these structures result either directly or indirectly from metabolic processes that alter the degree of unsaturation of the lipid. Different metabolic regimes in different plants produce these altered lipids, and either domestication of exotic plant species or modification of agronomically adapted species is usually required to economically produce large amounts of the desired lipid.

Plant lipids find their major use as edible oils in the form of triacylglycerols. The specific performance and health attributes of edible oils are determined largely by their fatty acid composition. Most vegetable oils derived from commercial plant varieties are composed primarily of palmitic (16:0), stearic (18:0), oleic (18:1), linoleic (18:2) and linolenic (18:3) acids. Palmitic and stearic acids are, respectively, 16- and 18-carbon-long, saturated fatty acids. Oleic, linoleic, and linolenic acids are 18-carbon-long, unsaturated fatty acids containing one, two, and three double bonds, respectively. Oleic acid is referred to as a mono-unsaturated fatty acid, while linoleic and linolenic acids are referred to as poly-unsaturated fatty acids.

Many recent research efforts have examined the role that saturated and unsaturated fatty acids play in reducing the risk of coronary heart disease. In the past, it was believed that mono-unsaturates, in contrast to saturates and poly-unsaturates, had no effect on serum cholesterol and coronary heart disease risk. Several recent human clinical studies suggest that diets high in mono-unsaturated fat and low in saturated fat may reduce the "bad" (low-density lipoprotein) cholesterol while maintaining the "good" (high-density lipoprotein) cholesterol (Mattson et al., *Journal of Lipid Research*(1985) 26:194–202).

A vegetable oil low in total saturates and high in mono-unsaturates would provide significant health benefits to consumers as well as economic benefits to oil processors. For specialized uses, high levels of poly-unsaturates can be desirable. Linoleate and linolenate are essential fatty acids in human diets, and an edible oil high in these fatty acids can be used for nutritional supplements, for example in baby foods.

The biosynthesis of the major plant lipids has been the focus of much research (Browse et al., *Ann. Rev. Plant Physiol. Mol. Biol.* (1991) 42:467–506). These studies show that, with the notable exception of the soluble stearoyl-acyl carrier protein desaturase, the controlling steps in the production of unsaturated fatty acids are largely catalyzed by membrane-associated fatty acid desaturases. Desaturation reactions occur in plastids and in the endoplasmic reticulum using a variety of substrates including galactolipids, sulfolipids, and phospholipids Genetic and physiological analyses of *Arabidopsis thaliana* nuclear mutants defective in various fatty acid desaturation reactions indicates that most of these reactions are catalyzed by enzymes encoded at single genetic loci in the plant. These investigations have demonstrated the role of delta-12 desaturase and delta-15 desaturase activities in the production of linoleate and linolenate from 2-oleoyl-phosphatidylcholine and 2-linoleoyl-phosphatidylcholine, respectively (Wang et al., *Plant Physiol. Biochem.* (1988) 26:777–792). Thus, modification of the activities of these enzymes represents an attractive target for altering the levels of lipid unsaturation by genetic engineering.

The cloning and characterization of wild-type delta-12 fatty acid desaturases has been reported (Okuley, et al., *Plant Cell* (1994) 6:147–158). However, there are no teachings concerning plants having seed-specific expression of mutant delta-12 or delta-15 fatty acid desaturase gene products. Furthermore, no methods have been described for altering the fatty acid composition of plants using nucleic aced constructs expressing a mutant delta-12 or a mutant delta-15 fatty acid desaturase.

SUMMARY OF THE INVENTION

Applicants have discovered a means to control the nature and levels of unsaturated fatty acids in plants. Nucleic acid fragments from cDNAs or genes encoding mutant fatty acid desaturases are used to create chimeric genes. The chimeric genes may be used to transform various plants to modify the fatty acid composition of the plant or the oil produced by the plant. The invention comprises nucleic acid constructs containing mutant microsomal delta-12 or mutant microsomal delta-15 fatty acid desaturase coding sequences, which are operably linked in sense orientation to at least one regulatory sequence. Such a construct is effective for altering fatty acid composition of seeds when the construct is introduced into a plant. In one embodiment, a mutant coding sequence for a delta-12 fatty acid desaturase comprises the mutation in the sequence of SEQ ID NO:3.

The invention further comprises seeds, plants and plant lines having a recombinant nucleic acid construct containing at least one regulatory sequence linked in sense orientation to a mutant delta-12 or mutant delta-15 fatty acid desaturase. The mutant chimeric gene preferentially is expressed in seeds and results in an altered fatty acid composition in seeds of such plants. A plant expressing a mutant delta-12 desaturase gene preferably has a reduced level of linoleic acid in seeds. A plant expressing a mutant delta-15 desaturase gene preferably has a reduced level of α-linolenic acid in seeds. If desired, a plant of the invention may express both a mutant delta-12 and a mutant delta-15 fatty acid desaturase, resulting in the reduction of both linoleic acid and α-linolenic acid in seeds.

Yet another embodiment of the invention involves a method of producing seed oil containing altered levels of unsaturated fatty acids comprising: (a) transforming a plant cell with a chimeric gene described above; (b) growing sexually mature plants from the transformed plant cells of step (a); (c) screening progeny seeds from the sexually mature plants of step (b) for the desired levels of unsaturated fatty acids, and (d) processing the progeny seed of step (c) to obtain seed oil containing altered levels of the unsaturated fatty acids. Preferred plant cells and oils are derived from soybean, rapeseed, sunflower, cotton, cocoa, peanut, safflower, coconut, flax, oil palm, and corn. Preferred methods of transforming such plant cells would include the use of Ti and Ri plasmids of *Agrobacterium*, electroporation, and high-velocity ballistic bombardment.

Yet another aspect of the invention involves a method of producing seeds having altered fatty acid composition. The method comprises the step of introducing a recombinant nucleic acid construct into a plant (i.e., transforming a plant). The construct comprises one or more seed-specific regulatory sequences operably linked in sense orientation to a mutant delta-12 fatty acid desaturase gene or a mutant delta-15 fatty acid desaturase gene. After obtaining transgenic progeny, those transformed plants that produce seeds having an altered fatty acid composition are identified. Suitable plants for transformation include, for example, soybean, rapeseed, sunflower, safflower, castor bean and corn. Suitable methods of transforming such plants include, for example, *Agrobacterium*—mediated methods, electroporation, and microprojectile bombardment.

The invention also is embodied in a method of RFLP breeding to obtain altered levels of oleic acids in the seed oil of oil producing plant species. This method involves (a) making a cross between two varieties of oil producing plant species differing in the oleic acid trait; (b) making a Southern blot of restriction enzyme digested genomic DNA isolated from several progeny plants resulting from the cross; and (c) hybridizing the Southern blot with the radiolabelled nucleic acid fragments encoding the mutant fatty acid desaturases or desaturase-related enzymes.

The invention is also embodied in a method of RFLP mapping that uses the isolated mutant microsomal delta-12 desaturase cDNA or related genomic fragments described herein.

Another embodiment of the instant invention is a method of genotyping plants containing either a mutant or wild-type form of the delta-12 desaturase gene by PCR amplification of genomic DNA using gene-specific primers. This method is capable of discriminating genes that differ by only one or a few nucleotides, thus affording a means for detecting plants containing the mutant delta-12 desaturase.

Another aspect of the invention comprises vegetable oil extracted from seeds of plants disclosed herein. Such a vegetable oil contains an altered fatty acid composition, e.g., a decreased level of α-linolenic acid, a decreased level of linoleic acid, or an increased level of oleic acid, based on total fatty acid composition.

BRIEF DESCRIPTION OF THE SEQUENCE DESCRIPTIONS

The invention can be more fully understood from the following detailed description and the Sequence Descriptions which form a part of this application. The Sequence Descriptions contain the three letter codes for amino acids as defined in 37 C.F.R. 1.822 which are incorporated herein by reference.

SEQ ID NO:1 shows the 5' to 3' nucleotide sequence of 1464 base pairs of the *Brassica napus* cDNA which encodes the wild type D form of microsomal delta-12 desaturase in plasmid pCF2–165d.

SEQ ID NO:2 is the 384 amino acid protein sequence deduced from the open reading frame in SEQ ID NO:1.

SEQ ID NO:3 shows the 5' to 3' cDNA nucleotide sequence of a mutant D form of microsomal delta-12 fatty acid desaturase from *Brassica napus* IMC129 Nucleotides 1–3 are the initiation codon and nucleotides 1153–1155 are the termination codon.

SEQ ID NO:4 is the 384 amino acid protein sequence deduced from the open reading frame of SEQ ID NO 3.

SEQ ID NO:5 shows the 5' to 3' cDNA nucleotide sequence of the wild-type F form of microsomal delta-12 fatty acid desaturase in *Brassica napus*. Nucleotides 1–3 are the initiation codon and nucleotides 1153–1155 are the termination codon.

SEQ ID NO:6 is the 384 amino acid protein sequence deduced from the open reading frame of SEQ ID NO:5.

SEQ ID NO:7 shows the 5' to 3' cDNA nucleotide sequence of a mutant F form of microsomal delta-12 fatty acid desaturase from *Brassica napus* IMC Q508. Nucleotides 1–3 are the initiation codon and nucleotides 1153–1155 are the termination codon.

SEQ ID NO:8 is the 384 amino acid protein sequence deduced from the open reading frame of SEQ ID NO:7.

SEQ ID NO:9 is the upstream (5') primer used for isolation of the D form of microsomal delta-12 fatty acid desaturase gene from *Brassica napus*.

SEQ ID NO:10 is the downstream (3') primer used for isolation of the D form of microsomal delta-12 fatty acid desaturase gene from *Brassica napus*.

SEQ ID NO:11 is the upstream (5') primer used for isolation of the F form of microsomal delta-12 fatty acid desaturas gene in *Brassica napus*.

SEQ ID NO:12 is the downstream (3') primer used for isolation of the F form of microsomal delta-12 fatty acid desaturase gene in *Brassica napus*.

SEQ ID NO:13 is the upstream (5') primer used for gene-specific detection of the wild type D form of microsomal delta-12 fatty acid desaturase gene in *Brassica napus*.

SEQ ID NO:14 is the upstream (5') primer used for gene-specific detection of the mutant D form of microsomal delta-12 fatty acid desaturase gene in *Brassica napus*.

SEQ ID NO:15 is the modified upstream (5') primer used for gene-specific detection of the wild type D form of microsomal delta-12 fatty acid desaturase gene in *Brassica napus*.

SEQ ID NO:16 is the modified upstream (5') primer used for gene-specific detection of the mutant D form of microsomal delta-12 fatty acid desaturase gene in *Brassica napus*.

SEQ ID NO:17 is a 5 amino acid sequence in which at least one mutation in the conserved three amino acids of this motif renders the delta-12 desaturase gene product non-functional.

BRIEF DESCRIPTION OF THE FIGURES

FIG. 3 shows the frequency distribution of seed oil linoleic acid (C18:2) content in transgenic *Brassica* T2 populations transformed with either a napin promoter linked in sense orientation to a wild-type microsomal delta-12 fatty acid desaturase D form coding sequence (WS127) or a phaseolin promoter linked to a mutant delta-12 fatty acid desaturase D form (WS201)

Figure 4:
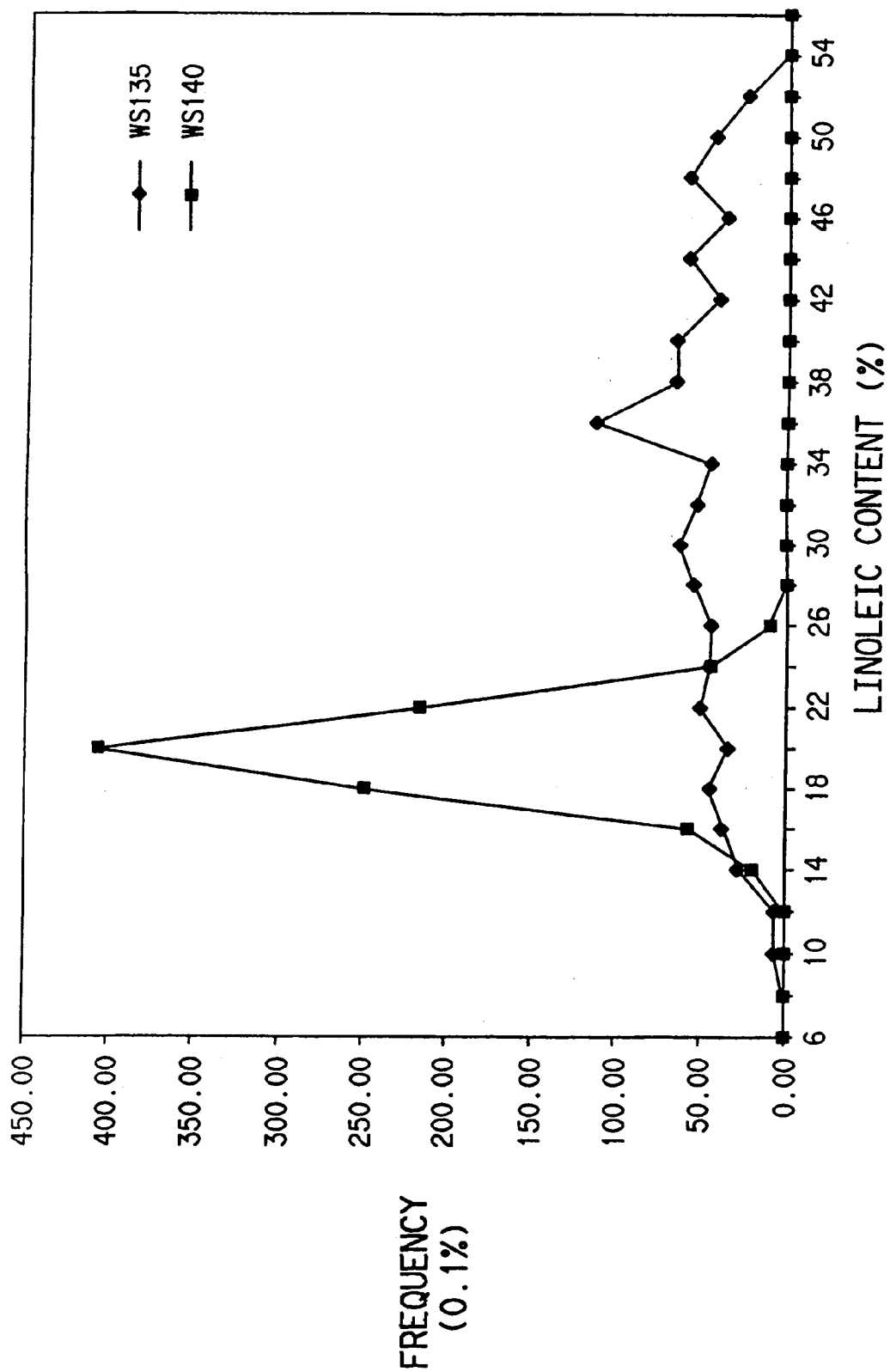

FIG. 4 shows the frequency distribution of seed oil linoleic acid content in transgenic Brassica T2 populations transformed with either a napin promoter linked in sense orientation to a mutant F form (WS140) delta-12 fatty acid desaturase coding sequence or a cruciferin promoter linked to a wild-type delta-12 fatty acid desaturase D form (WS135).

DETAILED DESCRIPTION OF THE INVENTION

Applicants have isolated nucleic acid fragments that encode mutant plant fatty acid desaturases and that are useful in modifying fatty acid composition in oil-producing species by genetic transformation.

Transfer of the nucleic acid fragments of the invention or a part thereof, along with suitable regulatory sequences that direct the transcription of their mRNA, into plants may result in production of decreased levels of unsaturated fatty acids in cellular lipids, including triacylglycerols.

The nucleic acid fragments of the invention can also be used as DNA diagnostic markers in plant genetic mapping and plant breeding programs.

The nucleic acid fragments of the invention or oligomers derived therefrom can also be used to isolate other related fatty acid desaturase genes using DNA, RNA, or a library of cloned nucleotide sequences from the same or different species by well known sequence-dependent protocols, including, for example, methods of nucleic acid hybridization and amplification by the polymerase chain reaction.

Definitions

In the context of this disclosure, a number of terms shall be used. Fatty acids are specified by the number of carbon atoms and the number and position of the double bond: the numbers before and after the colon refer to the chain length and the number of double bonds, respectively. The number following the fatty acid designation indicates the position of the double bond from the carboxyl end of the fatty acid with the "c" affix for the cis-configuration of the double bond. For example, palmitic acid (16:0), stearic acid (18:0), oleic acid (18:1, 9c), petroselinic acid (18:1, 6c), linoleic acid (18:2, 9c, 12c), γ-linolenic acid (18:3, 6c, 9c, 12c) and α-linolenic acid (18:3, 9c, 12c, 15c). Unless otherwise specified 18:1, 18:2 and 18:3 refer to oleic, linoleic and linolenic fatty acids. The term "fatty acid desaturase" used herein refers to an enzyme which catalyzes the breakage of a carbon-hydrogen bond and the introduction of a carbon—carbon double bond into a fatty acid molecule. The fatty acid may be free or esterified to another molecule including, but not limited to, acyl-carrier protein, coenzyme A, sterols and the glycerol moiety of glycerolipids. The term "glycerolipid desaturases" used here refers to a subset of the fatty acid desaturases that act on fatty acyl moieties esterified to a glycerol backbone. "Delta-12 desaturase" refers to a fatty acid desaturase that catalyzes the formation of a double bond between carbon positions 6 and 7 (numbered from the methyl end), (i.e., those that correspond to carbon positions 12 and 13 (numbered from the carbonyl carbon) of an 18 carbon-long fatty acyl chain. "Delta-15 desaturase" refers to a fatty acid desaturase that catalyzes the formation of a double bond between carbon positions 3 and 4 (numbered from the methyl end), (i.e., those that correspond to carbon positions 15 and 16 (numbered from the carbonyl carbon) of an 18 carbon-long fatty acyl chain. Examples of fatty acid desaturases include, but are not limited to, the microsomal delta-12 and delta-15 desaturases that act on phosphatidylcholine lipid substrates; the chloroplastic or plastid delta-12 and delta-15 desaturases that act on phosphatidyl glycerol and galactolipids; and other desaturases that act on such fatty acid substrates such as phospholipids, galactolipids, and sulfolipids. "Microsomal desaturase" refers to the cytoplasmic location of the enzyme, while "chloroplast desaturase" and "plastid desaturase" refer to the plastid location of the enzyme. These fatty acid desaturases may be found in a variety of organisms including, but not limited to, higher plants, diatoms, and various eukaryotic and prokaryotic microorganisms such as fungi and photosynthetic bacteria and algae. The term "homologous fatty acid desaturases" refers to fatty acid desaturases that catalyze the same desaturation on the same lipid substrate. Thus, microsomal delta-15desaturases, even from different plant species, are homologous fatty acid desaturases. The term "heterologous fatty acid desaturases" refers to fatty acid desaturases that catalyze desaturations at different positions and/or on different lipid substrates. Thus, for example, microsomal delta-12 and delta-15 desaturases, which act on phosphatidylcholine lipids, are heterologous fatty acid desaturases, even when from the same plant. Similarly, microsomal delta-15 desaturase, which acts on phosphatidylcholine lipids, and chloroplast delta-15 desaturase, which acts on galacto-lipids, are heterologous fatty acid desaturases, even when from the same plant. It should be noted that these fatty acid desaturases have never been isolated and characterized as proteins. Accordingly, the terms such as "delta-12 desaturase" and "delta-15 desaturase" are used as a convenience to describe the proteins encoded by nucleic acid fragments that have been isolated based on the phenotypic effects caused by their disruption. They do not imply any catalytic mechanism. For example, delta-12 desaturase refers to the enzyme that catalyzes the formation of a double bond between carbons 12 and 13 of an 18 carbon fatty acid irrespective of whether it "counts" the carbons from the methyl, carboxyl end, or the first double bond.

The term "nucleic acid" refers to a large molecule which can be single-stranded or double-stranded, composed of monomers (nucleotides) containing a sugar, a phosphate and either a purine or pyrimidine. A "nucleic acid fragment" is a fraction of a given nucleic acid molecule. In higher plants, deoxyribonucleic acid (DNA) is the genetic material while ribonucleic acid (RNA) is involved in the transfer of the information in DNA into proteins. A "genome" is the entire body of genetic material contained in each cell of an organism. The term "nucleotide sequence" refers to the sequence of DNA or RNA polymers, which can be single- or double-stranded, optionally containing synthetic, non-natural or altered nucleotide bases capable of incorporation into DNA or RNA polymers. The term "oligomer" refers to short nucleotide sequences, usually up to 100 bases long.

From time to time, the term "FAD2" may be used herein as a shorthand notation for a nucleotide sequence encoding a wild type microsomal delta-12 fatty acid desaturase enzyme, and the term "fad2" may be used herein as a shorthand notation for a nucleotide sequence encoding a mutant form of a microsomal delta-12 fatty acid desaturase enzyme.

As used herein, the term "homologous to" refers to the relatedness between the nucleotide sequence of two nucleic acid molecules or between the amino acid sequences of two protein molecules. Estimates of such homology are provided by either DNA—DNA or DNA-RNA hybridization under conditions of stringency as is well understood by those skilled in the art (Hames and Higgins, Eds. (1985) Nucleic Acid Hybridisation, IRL Press, Oxford, U.K.); or by the comparison of sequence similarity between two nucleic acids or proteins, such as by the method of Needleman et al. (J. Mol. Biol. (1970) 48:443–453). As used herein, "essentially similar" refers to DNA sequences that may involve base changes that do not cause a change in the encoded amino acid, or which involve base changes which may alter one or more amino acids, but do not affect the functional properties of the protein encoded by the DNA sequence. It is therefore understood that the invention encompasses more than the specific exemplary sequences. Modifications to the sequence, such as deletions, insertions, or substitutions in the sequence which produce silent changes that do not substantially affect the functional properties of the resulting protein molecule are also contemplated. For example, alteration in the gene sequence which reflect the degeneracy of the genetic code, or which results in the production of a chemically equivalent amino acid at a given site, are contemplated; thus, a codon for the amino acid alanine, a hydrophobic amino acid, may be substituted by a codon encoding another hydrophobic amino acid residue such as glycine, valine, leucine, or isoleucine. Similarly, changes which result in substitution of one negatively charged residue for another, such as aspartic acid for glutamic acid, or one positively charged residue for another, such as lysine for arginine, can also be expected to produce a biologically equivalent product. Nucleotide changes which result in alteration of the N-terminal and C-terminal portions of the protein molecule would also not be expected to alter the activity of the protein. Each of the proposed modifications is well within the routine skill in the art, as is determination of retention of biological activity of the encoded products.

"Gene" refers to a nucleic acid fragment that expresses a specific protein, including regulatory sequences preceding (5' non-coding) and following (3' non-coding) the coding region. "Fatty acid desaturase gene" refers to a nucleic acid fragment that expresses a protein with fatty acid desaturase activity. "Native" gene refers to an isolated gene with its own regulatory sequences as found in nature. "Chimeric gene" refers to a gene that comprises heterogeneous regulatory and coding sequences not found in nature. "Endogenous" gene refers to the native gene normally found in its natural location in the genome and is not isolated. A "foreign" gene refers to a gene not normally found in the host organism but that is introduced by gene transfer. "Pseudogene" refers to a genomic nucleotide sequence that does not encode a functional enzyme. "Mutant gene" refers to a gene comprising one or more nucleotides that have been altered when compared to the wild-type nucleotide sequence, resulting in a change to the amino acid sequence and functional properti s of the encoded protein.

"Coding sequence" refers to a DNA sequence that codes for a specific protein and excludes the non-coding sequences. It may constitute an "uninterrupted coding sequence", i.e., lacking an intron or it may include one or more introns bounded by appropriate splice junctions. An "intron" is a nucleotide sequence that is transcribed in the primary transcript but that is removed through cleavage and re-ligation of the RNA within the cell to create the mature mRNA that can be translated into a protein.

"Initiation codon" and "termination codon" refer to a unit of three adjacent nucleotides in a coding sequence that specifies initiation and chain termination, respectively, of protein synthesis (mRNA translation). "Open reading frame" refers to the coding sequence uninterrup-ted by introns between initiation and termination codons that encodes an amino acid sequence.

"RNA transcript" refers to the product resulting from RNA polymerase-catalyzed transcription of a DNA sequence. When the RNA transcript is a perfect complementary copy of the DNA sequence, it is referred to as the primary transcript or it may be a RNA sequence derived from posttranscriptional processing of the primary transcript and is referred to as the mature RNA. "Messenger RNA (mRNA)" refers to the RNA that is without introns and that can be translated into protein by the cell. "cDNA" refers to a double-stranded DNA that is complementary to and derived from mRNA. "Sense" RNA refers to RNA transcript that includes the mRNA. "Antisense RNA" refers to a RNA transcript that is complementary to all or part of a target primary transcript or mRNA and that blocks the expression of a target gene by interfering with the processing, transport and/or translation of its primary transcript or mRNA. The complementarity of an antisense RNA may be with any part of the specific gene transcript, i.e., at the 5' non-coding sequence, 3' non-coding sequence, introns, or the coding sequence. In addition, as used herein, antisense RNA may contain regions of ribozyme sequences that increase the efficacy of antisense RNA to block gene expression. "Ribozyme" refers to a catalytic RNA and includes sequence-specific endoribonucleases.

As used herein, "suitable regulatory sequences" refer to nucleotide sequences in native or chimeric genes that are located upstream (5'), within, and/or downstream (3') to the nucleic acid fragments of the invention, which control the expression of the nucleic acid fragments of the invention. The term "expression", as used herein, refers to the transcription and stable accumulation of the sense (mRNA) derived from the nucleic acid fragment(s) of the invention that, in conjunction with the protein apparatus of the cell, results in altered levels of the fatty acid desaturase(s). Expression or overexpression of the gene involves transcription of the gene and translation of the mRNA into precursor or mature fatty acid desaturase proteins. "Altered levels" refers to the production of gene product(s) in transgenic organisms in amounts or proportions that differ from that of normal or non-transformed organisms.

"Promoter" refers to a DNA sequence in a gene, usually upstream (5') to its coding sequence, which controls the expression of the coding sequence by providing the recognition for RNA polymerase and other factors required for proper transcription. Promoters may also contain DNA sequences that are involved in the binding of protein factors which control the effectiveness of transcription initiation in response to physiological or developmental conditions. It may also contain enhancer elements. An "enhancer" is a DNA sequence which can stimulate promoter activity. It may be an innate element of the promoter or a heterologous element inserted to enhance the level and/or tissue-specificity of a promoter. "Constitutive promoters" refers to those that direct gene expression in all tissues and at all times. "Tissue-specific" or "development-specific" promoters as referred to herein are those that direct gene expression almost exclusively in specific tissues, such as leaves or seeds, or at specific development stages in a tissue, such as in early or late embryogenesis, respectively.

The "3' non-coding sequences" refers to the DNA sequence portion of a gene that contains a polyadenylation signal and any other regulatory signal capable of affecting mRNA processing or gene expression. The polyadenylation signal is usually characterized by affecting the addition of polyadenylic acid tracts to the 3' end of the mRNA precursor.

"Transformation" herein refers to the transfer of a foreign gene into the genome of a host organism and its genetically stable inheritance. "Restriction fragment length polymorphism" (RFLP) refers to different sized restriction fragment lengths due to altered nucleotide sequences in or around variant forms of genes. "Molecular breeding" refers to the use of DNA-based diagnostics, such as RFLP, RAPDs, and PCR in breeding. "Fertile" refers to plants that are able to propagate sexually.

"Plants" refer to photosynthetic organisms, both eukaryotic and prokaryotic, whereas the term "Higher plants" refers to eukaryotic plants. "Oil-producing species" herein refers to plant species which produce and store triacylglycerol in specific organs, primarily in seeds. Such species include soybean (*Glycine max*), rapeseed and canola (including *Brassica napus*, B. *campestris*), sunflower (*Helianthus annus*), cotton (*Gossypium hirsutum*), corn (*Zea mays*), cocoa (*Theobroma cacao*), safflower (*Carthamus tinctorius*), oil palm (*Elaeis guineensis*), coconut palm (*Cocos nucifera*), flax (*Linum usitatissimum*), (castor (*Ricinus communis*)) and peanut (*Arachis hypogaea*). The group also includes non-agronomic species which are useful in developing appropriate expression vectors such as tobacco, rapid cycling *Brassica* species, and *Arabidopsis thaliana*, and wild species which may be a source of unique fatty acids.

"Progeny" includes descendants of a particular plant or plant line, e.g., seeds and plants of F1, F2, F3, and subsequent generations, or seeds and plants of backcrossed populations BC1, BC2, BC3 and subsequent generations.

"Sequence-dependent protocols" refer to techniques that rely on a nucleotide sequence for their utility. Examples of sequence-dependent protocols include, but are not limited to, the methods of nucleic acid and oligomer hybridization and methods of DNA and RNA amplification such as are exemplified in various uses of the polymerase chain reaction (PCR).

Various solutions used in the experimental manipulations are referred to by their common names such as "SSC", "SSPE", "Denhardt's solution", etc. The composition of these solutions may be found by reference to Appendix B of Sambrook, et al. (Molecular Cloning, A Laboratory Manual, 2nd ed. (1989), Cold Spring Harbor Laboratory Press).

Availability and Relatedness of Wild-Type Microsomal Delta-12 and Delta-15 Fatty Acid Desaturases U.S. patent application Ser. No. 08/262,401, incorporated herein by reference, describes the isolation and characterization of cDNAs encoding wild-type microsomal delta-12 fatty acid desaturases from a number of plant species, including *Arabidopsis thaliana, Brassica napus, Glycine max, Zea mays* and Castor bean. Moreover, that application demonstrates successful alteration of fatty acid content of oils from seeds obtained from transgenic plants expressing sense or antisense mRNAs encoding microsomal delta-12 fatty acid desaturases.

Alignments of protein sequences of plant microsomal fatty acid delta-12 desaturases and plant delta-15 desaturases [microsomal and plastid delta-15 desaturases from *Arabidopsis* and *Brassica napus*, WO 9311245] allows identification of amino acid sequences conserved between the different desaturases (Table 1).

TABLE 1

Amino Acid Sequence Conserved Between Plant Microsomal Delta-12 Desaturases and Microsomal and Plastid Delta-15 Desaturases

| Region | Conserved AA Positions in SEQ ID NO:2 of USSN 08/262,401 | Consensus Conserved AA Sequence in $\Delta^{12}$ Desaturases | Consensus Conserved AA Sequence in $\Delta^{15}$ Desaturases | Consensus AA Sequence |
|---|---|---|---|---|
| A | 39–44 | AIPPHC (SEQ ID NO:18) | AIPKHC (SEQ ID NO:19) | AIP(P/K)HC (SEQ ID NO:20) |
| B | 86–90 | WP(L/I)YW (SEQ ID NO:21) | WPLYW (SEQ ID NO:22) | WP(L/I)YW (SEQ ID NO:21) |
| C | 104–109 | AHECGH (SEQ ID NO:23) | GHDCGH (SEQ ID NO:24) | (A/G)H(D/E)CGH (SEQ ID NO:25) |
| D | 130–134 | LLVPY (SEQ ID NO:26) | ILVPY (SEQ ID NO:27) | (L/I)LVPY (SEQ ID NO:28) |
| E | 137–142 | WKYSHR (SEQ ID NO:29) | WRISHR (SEQ ID NO:30) | W(K/R)(Y/I)SHR (SEQ ID NO:31) |
| F | 140–145 | SHRRHH (SEQ ID NO:32) | SHRTHH (SEQ ID NO:33) | SHR(R/T)HH (SEQ ID NO:34) |
| G | 269–274 | ITYLQ (SEQ ID NO:35) | VTYLH (SEQ ID NO:36) | (I/V)TYL(Q/H) (SEQ ID NO:37) |
| H | 279–282 | LPHY (SEQ ID NO:38) | LPWY (SEQ ID NO:39) | LP(H/W)Y (SEQ ID NO:40) |
| I | 289–294 | WL(R/K)GAL (SEQ ID NO:41) | YLRGGL (SEQ ID NO:42) | (W/Y)L(R/K)G(A/G)L (SEQ ID NO:43) |
| J | 296–302 | TVDRDYG (SEQ ID NO:44) | TLDRDYG (SEQ ID NO:45) | T(V/L)DRDYG (SEQ ID NO:46) |
| K | 314–321 | THVAHHLF (SEQ ID NO:47) | THVIHHLF (SEQ ID NO:48) | THV(A/I)HHLF (SEQ ID NO:49) |
| L | 318–327 | HHLFSTMPHY (SEQ ID NO:50) | HHLFPQIPHY (SEQ ID NO:51) | HHLF(S/P)(T/Q)(I/M)PHY (SEQ ID NO:52) |

Table 1 shows twelve regions of conserved amino acid sequences, designated A–L (column 1), whose positions in SEQ ID NO:2 of U.S. Ser. No. 08/262,401 are shown in column 2. The consensus sequences for these regions in plant delta-12 fatty acid desaturases and plant delta-15 fatty acid desaturases are shown in columns 3 and 4, respectively; amino acids are shown by standard abbreviations, the underlined amino acids are conserved between the delta-12 and the delta-15 desaturases, and amino acids in brackets represent substitutions found at that position. The consensus sequence of these regions are shown in column 5. These short conserved amino acids and their relative positions further confirm that the isolated isolated cDNAs encode a fatty acid desaturase.

Inhibition of Plant Target Genes By Dominant Negative Suppression

In one embodiment, transgenic plants according to the invention contain an introduced nucleic acid construct that comprises at least a portion of a mutant delta-12 or delta-15 desaturase coding sequence. Surprisingly, a construct comprising a mutant delta-12 desaturase or delta-15 desaturase coding sequence, operably linked in sense orientation to one or more regulatory sequences, has been found to inhibit the corresponding endogenous fatty acid desaturase activity in plants which contain such a construct. This phenomenon has been termed dominant negative suppression.

The basis for the phenomenon of dominant negative suppression is not understood. One possible explanation is that the delta-12 desaturase gene product exists as a dimer in vivo. If so, a dimer consisting of the mutant gene product and the wild-type gene product may be non-functional. Regardless of the actual mechanism by which dominant negative suppression operates, the observation that transformation of plants with a mutant delta-12 desaturase gene results in a large proportion of the transgenic progeny having endogenous wild-type enzyme activity inhibited by expression of the mutant gene can be used to advantage. For example, the phenomenon of dominant negative suppression can be used to alter plant desaturase enzyme activity in a tissue-specific manner. The phenomenon may also allow transformation experiments to be carried out in which a higher proportion of the resulting transgenic plants have a desired altered fatty acid profile and allow transgenic plants having desired fatty acid profiles to be more readily obtained.

Preferred constructs contain, in addition, at least one regulatory sequence operably linked in the sense orientation to the mutant coding sequence. Regulatory sequences typically do not themselves code for a gene product. Instead, regulatory sequences affect the expression level of the mutant coding sequence.

In preferred embodiments, regulatory sequences for dominant negative suppression are tissue-specific, i.e., the mutant desaturase gene product is preferentially expressed in certain plant tissues and expressed at low levels or not at all in the remaining tissues of the plant. Suitable tissue-specific regulatory sequences include those that permit expression preferentially in developing seeds. Seed-specific regulatory sequences preferably stimulate or induce levels of mutant desaturase gene product expression that coincide with the levels of wild-type desaturase gene product expression.

Dominant negative suppression plants according to the invention preferably yield seeds containing an altered fatty acid profile. For example, oil obtained from seeds of such plants may have from about 69% to about 90% oleic acid, based on the total fatty acid composition of the seed. Such oil preferably has from about 74% to about 90% oleic acid, more preferably from about 80% to about 90% oleic acid. In some embodiments, oil extracted from seeds produced by plants of the invention may have from about 3% to about 5% saturated fatty acids, based on total fatty acid composition of the seeds. In some embodiments, oil extracted from seeds of the invention may have from about 1% to about 10% linoleic acid, or from about 1% to about 10% α-linolenic acid.

After a recombinant nucleic acid construct, comprising a mutant microsomal delta-12 fatty acid desaturase coding sequence operably linked in the sense orientation to one or more regulatory sequences, is introduced into a plant, seeds of transgenic plants are grown and either selfed or outcrossed. Progeny are analyzed to identify those individuals having endogenous wild-type delta-12 fatty acid desaturase activity inhibited by dominant negative suppression as discussed above.

Method similar to those described above are used to make delta-15 desaturase dominant negative suppression constructs, comprising a mutant delta-15 desaturase gene operably linked to at least one regulatory sequence. Transformation of a plant with such a construct will result in dominant negative suppression of endogenous delta-15 desaturase activity in transgenic progeny and in a decreased level of α-linolenic acid in homozygous dominant suppression lines. Such lines will have from about <1% to about 10% α-linolenic acid, preferably from about <1% to about 5%, based on total seed fatty acid composition.

In one embodiment of the invention, a plant contains a mutant delta-12 fatty acid desaturase and a mutant delta-15 fatty acid desaturase, both of which are expressed preferentially in seeds. Such a plant can be produced from the cross of single mutant plants, followed by outcrossing or selfing in order to obtain progeny seeds carrying both mutant chimeric genes. Progeny seeds can be screened in order to identify those seeds carrying both mutant genes. Alternatively, seed-specific defects in delta-12 desaturase and delta-15 desaturase may be introduced into a wild-type plant by transformation, simultaneously or sequentially, with one or more dominant negative suppression constructs for delta-12 desaturase and delta-15 desaturase, each driven by suitable regulatory sequences. Other similar methods to construct double mutant plants will be recognized by those of skill in the art.

Double mutant plants can have more extreme fatty acid profiles in seeds than the single mutant plants, e.g., the double mutant phenotype can result in significantly lower levels of α-linolenic acid in seeds than the single mutant delta-15 desaturase plant phenotype. Thus, by combining seed-specific inhibition of microsomal delta-12 desaturase with seed-specific inhibition of microsomal delta-15 desaturase, one can obtain levels of seed α-linolenic acid that are as low or lower than those in a single mutant without adversely affecting desirable properties. The decreased levels of α-linolenic acid in the double homozygotes may be associated with increased levels of oleic acid and decreased levels of saturates and linoleic acid.

Selection of Hosts, Promoters and Enhancers

A preferred class of heterologous hosts for the expression of the nucleic acid fragments of the invention are eukaryotic hosts, particularly the cells of higher plants. Particularly preferred among the higher plants are the oil-producing species, such as soybean (*Glycine max*), rapeseed (including *Brassica napus, B. campestris*), sunflower (*Helianthus annus*), cotton (*Gossypium hirsutum*), corn (*Zea mays*), cocoa (*Theobroma cacao*), safflower (*Carthamus tincto-* rius), oil palm (*Elaeis guineensis*), coconut palm (*Cocos nucifera*), flax (*Linum usitatissimum*), and peanut (*Arachis hypogaea*).

Expression in plants will use regulatory sequences functional in such plants. The expression of foreign genes in plants is well-established (De Blaere et al., *Meth. Enzymol.* (1987) 153:277–291). The source of the promoter chosen to drive the expression of the fragments of the invention is not critical provided it has sufficient transcriptional activity to accomplish the invention by increasing or decreasing, respectively, the level of translatable mRNA for the fatty acid desaturases in the desired host tissue. Preferred promoters include (a) strong constitutive plant promoters, such as those directing the 19S and 35S transcripts in cauliflower mosaic virus (bdell et al., *Nature* (1985) 313:810–812; Hull et al., *Virology* (1987) 86:482–493),(b) tissue- or developmentally-specific promoters, and (c) other transcriptional promoter systems engineered in plants, such as those using bacteriophage T7 RNA polymerase promoter sequences to express foreign genes. Examples of tissue-specific promoters are the light-inducible promoter of the small subunit of ribulose 1,5-bis-phosphate carboxylase (if expression is desired in photosynthetic tissues), the maize zein protein promoter (Matzke et al., *EMBO J.* (1984) 3:1525–1532), and the chlorophyll a/b binding protein promoter (Lampa et al., *Nature* (1986) 316:750–752).

Particularly preferred promoters are those that allow seed-specific expression. This may be especially useful since seeds are the primary source of vegetable oils and also since seed-specific expression will avoid any potential deleterious effect in non-seed tissues. Examples of seed-specific promoters include, but are not limited to, the promoters of seed storage proteins, which can represent up to 90% of total seed protein in many plants. The seed storage proteins are strictly regulated, being expressed almost exclusively in seeds in a highly tissue-specific and stage-specific manner (Higgins et al., *Ann. Rev. Plant Physiol.* (1984) 35:191–221; Goldberg et al., *Cell* (1989) 56:149–160). Moreover, different seed storage proteins may be expressed at different stages of seed development.

Expression of seed-specific genes has been studied in great detail (See reviews by Goldberg et al., *Cell* (1989) 56:149–160 and Higgins et al., *Ann. Rev. Plant Physiol.* (1984) 35:191–221). There are currently numerous examples of seed-specific expression of seed storage protein genes in transgenic dicotyledonous plants. These include genes from dicotyledonous plants for bean β-phaseolin (Sengupta-Gopalan et al., *Proc. Natl. Acad. Sci.* USA (1985) 82:3320–3324; Hoffman et al., *Plant Mol. Biol.* (1988) 11:717–729), bean lectin (Voelker et al., *EMBO J.* (1987) 6:3571–3577), soybean lectin (Okamuro et al., *Proc. Natl. Acad. Sci.* USA (1986) 83:8240–8244), soybean Kunitz trypsin inhibitor (Perez-Grau et al., *Plant Cell* (1989) 1:095–1109), soybean β-conglycinin (Beachy et al., *EMBO J.* (1985) 4:3047–3053; pea vicilin (Higgins et al., *Plant Mol. Biol.* (1988) 11:683–695), pea convicilin (Newbigin et al., *Planta* (1990) 180:461–470), pea legumin (Shirsat et al., *Mol. Gen. Genetics* (1989) 215:326–331); rapeseed napin (Radke et al., *Theor. Appl. Genet.* (1988) 75:685–694) as well as genes from monocotyledonous plants such as for maize 15 kD zein (Hoffman et al., *EMBO J.* (1987) 6:3213–3221), maize 18 kD oleosin (Lee et al., *Proc. Natl. Acad. Sci.* USA (1991) 888:6181–6185), barley β-hordein (Marris et al., *Plant Mol. Biol.* (1988) 10:359–366) and wheat glutenin (Colot et al., *EMBO J.* (1987) 6:3559–3564). Moreover, promoters of seed-specific genes operably linked to heterologous coding sequences in chimeric gene constructs also maintain their temporal and spatial expression pattern in transgenic plants. Such examples include use of *Arabidopsis thaliana* 2S seed storage protein gene promoter to express enkephalin peptides in *Arabidopsis* and *B. napus* seeds (Vandekerckhove et al., *Bio/Technology*(1989) 7:929–932), bean lectin and bean β-phaseolin promoters to express luciferase (Riggs et al., *Plant Sci.* (1989) 63:47–57), and wheat glutenin promoters to express chloramphenicol acetyl transferase (Colot et al., *EMBO J.* (1987) 6:3559–3564).

Of particular use in the expression of the nucleic acid fragment of the invention will be the heterologous promoters from several soybean seed storage protein genes such as those for the Kunitz trypsin inhibitor (Jofuku et al., *Plant Cell* (1989) 1:1079–1093; glycinin (Nielson et al., *Plant Cell* (1989) 1:313–328), and β-conglycinin (Harada et al., *Plant Cell* (1989) 1:415–425). Promoters of genes for α- and β-subunits of soybean β-conglycinin storage protein will be particularly useful in expressing the mRNA or the antisense RNA in the cotyledons at mid- to late-stages of seed development (Beachy et al., *EMBO J.* (1985) 4:3047–3053) in transgenic plants. This is because there is very little position effect on their expression in transgenic seeds, and the two promoters show different temporal regulation. The promoter for the α-subunit gene is expressed a few days before that for the β-subunit gene. This is important for transforming rapeseed where oil biosynthesis begins about a week before seed storage protein synthesis (Murphy et al., *J. Plant Physiol.* (1989) 135:63–69).

Also of particular use will be promoters of genes expressed during early embryogenesis and oil biosynthesis. The native regulatory sequences, including the native promoters, of the fatty acid desaturase genes expressing the nucleic acid fragments of the invention can be used following their isolation by those skilled in the art. Heterologous promoters from other genes involved in seed oil biosynthesis, such as those for *B. napus* isocitrate lyase and malate synthase (Comai et al., *Plant Cell* (1989) 1:293–300), delta-9 desaturase from safflower (Thompson et al. *Proc. Natl. Acad. Sci.* USA (1991) 88:2578–2582) and castor (Shanklin et al., *Proc. Natl. Acad. Sci.* USA (1991) 88:2510–2514), acyl carrier protein (ACP) from *Arabidopsis*(Post-Beittenmiller et al., *Nucl. Acids Res.* (1989) 17:1777), *B. napus* (Safford et al., *Eur. J. Biochem.* (1988) 174:287–295), and *B. campestris* (Rose et al., *Nucl. Acids Res.* (1987) 15:7197), β-ketoacyl-ACP synthetase from barley (Siggaard-Andersen et al., *Proc. Natl. Acad. Sci.* USA (1991) 88:4114–4118), and oleosin from *Zea mays* (Lee et al., *Proc. Natl. Acad. Sci.* USA (1991) 88:6181–6185), soybean (Genbank Accession No: X60773) and *B. napus* (Lee et al., *Plant Physiol.* (1991) 96:1395–1397) will be of use. If the sequence of the corresponding genes is not disclosed or their promoter region is not identified, one skilled in the art can use the published sequence to isolate the corresponding gene and a fragment thereof containing the promoter. The partial protein sequences for the relatively-abundant enoyl-ACP reductase and acetyl-CoA carboxylase are also published (Slabas et al., *Biochim. Biophys. Acta* (1987) 877:271–280; Cottingham et al., *Biochim. Biophys. Acta* (1988) 954:201–207) and one skilled in the art can use these sequences to isolate the corresponding seed genes with their promoters. Similarly, the fragments of the present invention encoding fatty acid desaturases can be used to obtain promoter regions of the corresponding genes for use in expressing chimeric genes.

Attaining the proper level of expression of the nucleic acid fragments of the invention may require the use of different chimeric genes utilizing different promoters. Such chimeric genes can be transferred into host plants either together in a single expression vector or sequentially using more than one vector.

It is envisioned that the introduction of enhancers or enhancer-like elements into the promoter regions of either the native or chimeric nucleic acid fragments of the invention will result in increased expression to accomplish the invention. This would include viral enhancers such as that found in the 35S promoter (Odell et al., *Plant Mol. Biol.* (1988) 10:263–272), enhancers from the opine genes (Fromm et al., *Plant Cell* (1989) 1:977–984), or enhancers from any other source that result in increased transcription when placed into a promoter operably linked to a nucleic acid fragment of the invention.

Of particular importance is the DNA sequence element isolated from the gene for the α-subunit of β-conglycinin that can confer 40-fold seed-specific enhancement to a constitutive promoter (Chen et al., *Dev. Genet.* (1989) 10:112–122). One skilled in the art can readily isolate this element and insert it within the promoter region of any gene in order to obtain seed-specific enhanced expression with the promoter in transgenic plants. Insertion of such an element in any seed-specific gene that is expressed at different times than the β-conglycinin gene will result in expression in transgenic plants for a longer period during seed development.

The invention can also be accomplished by a variety of other methods to obtain the desired end. In one form, the invention is based on modifying plants to produce increased levels of mutant fatty acid desaturases by virtue of introducing more than one copy of the foreign gene containing the nucleic acid fragments of the invention. In some cases, the desired level of polyunsaturated fatty acids may require introduction of foreign genes for more than one kind of mutant fatty acid desaturase.

Any 3' non-coding region capable of providing a polyadenylation signal and other regulatory sequences that may be required for the proper expression of the nucleic acid fragments of the invention can be used to accomplish the invention. This would include 3' ends of the native fatty acid desaturase(s), viral genes such as from the 35S or the 19S cauliflower mosaic virus transcripts, from the opine synthesis genes, ribulose 1,5-bisphosphate carboxylase, or chlorophyll a/b binding protein. There are numerous examples in the art that teach the usefulness of different 3' non-coding regions.

Transformation Methods

Various methods of transforming cells of higher plants according to the present invention are available to those skilled in the art (see EPO Pub. 0 295 959 A2 and 0 318 341 A1). Such methods include those based on transformation vectors utilizing the Ti and Ri plasmids of *Agrobacterium spp.* It is particularly preferred to use the binary type of these vectors. Ti-derived vectors transform a wide variety of higher plants, including monocotyledonous and dicotyledonous plants (Sukhapinda et al., *Plant Mol. Biol.* (1987) 8:209–216; Potrykus, *Mol. Gen. Genet.* (1985) 199:183). Other transformation methods are available to those skilled in the art, such as direct uptake of foreign DNA constructs (see EPO Pub. 0 295 959 A2), techniques of electroporation (Fromm et al., *Nature* (1986) (London) 319:791) or highvelocity ballistic bombardment with metal particles coated with the nucleic acid constructs (Kline et al., *Nature* (1987) (London) 327:70). Once transformed, the cells can be regenerated by those skilled in the art.

Of particular relevance are the recently described methods to transform foreign genes into commercially important crops, such as rapeseed (De Block et al., *Plant Physiol.* (1989) 91:694–701), sunflower (Everett et al., *Bio/Technology* (1987) 5:1201), and soybean (Christou et al., *Proc. Natl. Acad. Sci* USA (1989) 86:7500–7504.

Application to Plant Breeding

The use of restriction fragment length polymorphism (RFLP) markers in plant breeding has been well-documented in the art (Tanksley et al., *Bio/Technology* (1989) 7:257–264). Thus, the nucleic acid fragments of the invention can be used as molecular markers for traits associated with mutant fatty acid desaturases. These traits will include altered levels of unsaturated fatty acids. The nucleic acid fragment of the invention can also be used to isolate the fatty acid desaturase gene from other mutant plants with altered levels of unsaturated fatty acids. Sequencing of these genes will reveal nucleotide differences that cause the alteration in levels of unsaturated fatty acids. Oligonucleotides designed around these differences may also be used in plant breeding as diagnostic markers to follow fatty acid variation. In one embodiment, oligonucleotides based on differences betwen wt and mutant Δ12 des may be used as molecular markers in breeding canola lines with variant oil profiles.

EXAMPLES

The present invention is further defined in the following Examples, in which all parts and percentages are by weight and degrees are Celsius, unless otherwise stated. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various usages and conditions. All publications, including patents and nonpatent literature, referred to in this specification are expressly incorporated by reference herein.

Example 1

Sequences of Mutant Delta-12 Fatty Acid Desaturases from *B. Napus*

Primers specific for the FAD2 structural gene were used to clone the entire open reading frame (ORF) of the D and F forms of the gene by reverse transcription-polymerase chain reaction (RT-PCR). The sequences of the primers used for isolation of the D form ORF of *B. napus* FAD2 gene are 5'-CATGGGTGCAGGTGGAAGAATGC-3'    (SEQ ID NO: 9); and

5'-GTTTCTTCTTTGCTTCATAAC-3'    (SEQ ID NO: 10).

The sequences of the primers used to clone the F form ORF of *B. napus* FAD2 gene are 5'-CATGGGTGCAGGTGGAAGAATGC3'    (SEQ ID NO: 11); and

5'-TCTTTCACCATCATCATATC-3'    (SEQ ID NO: 12).

RNA from seeds of three lines, IMC129, Q508 and Westar, was isolated by an acid guanidinium thiocyanate-phenol-chloroform extraction method (Chomczynski and Sacchi, 1987; *Analytical Biochemistry* 162, 156–159, 1987). The total RNA was used as a template for reverse transcription and PCR amplification by RNA PCR kit (Perkin Elm r). The RT-PCR amplified fragments were cloned into pGEM-T vector (Promega), and then used for nucleotide sequence determination. The DNA sequence of each gene from each line was determined from both strands by dideoxy sequencing by Sanger et al. (*Proc Natl Acad Sci* USA 74, 5463–5467).

The D gene of IMC129 contained a G to A transversion at nucleotide 316 (from the translation initiation codon) of the D gene in IMC 129, compared to the sequence of Westar. The transversion changes the codon at this position from GAG to AAG and results in a substitution of lysine for glutamic acid. The same base change was also detected in IMC129 when RNA from leaf tissue was used as template. The G to A mutation at nucleotide 316 was confirmed by sequencing several independent clones containing fragments amplified directly from genomic DNA of IMC129. These results eliminated the possibility of a rare mutation introduced during reverse transcription and PCR in the RT-PCR protocol. The mutation in the D form of delta-12 desaturase in IMC129 mapped to a conserved region of cloned delta-12 and delta-15 membrane bound desaturases (Table 5).

The sequence of the F form of delta-12 desaturase in IMC129 was the same as the F form of delta-12 desaturase in Westar.

For Q508, the sequence of the D form of delta-12 desaturase was the same as the D form of the IMC129 gene. This was expected, as Q508 was derived by mutagenesis of IMC129.

Sequence analysis of the Q508 F form of delta-12 desaturase revealed a T to A transition at nucleotide 515, compared to the wild-type Westar sequence. This mutation results in a change from a CTC codon to a CAC codon, substituting a histidine residue for the wild-type leucine residue.

TABLE 2

Alignment of Amino Acid Sequences of Cloned Canola Membrane Bound-Desaturases

| Desaturase Gene | Sequence[a] | Position[b] |
| --- | --- | --- |
| Canola-FAD2-D | HECGH (SEQ ID NO:53) | 110 |
| Canola-FAD2-F | HECGH (SEQ ID NO:53) | 110 |
| Canola-FAD6[c] | HDCAH (SEQ ID NO:54) | 171 |
| Canola-FAD3[d] | HDCGH (SEQ ID NO:55) | 97 |
| Canola-FAD7[e] | HDCGH (SEQ ID NO:55) | 126 |

[a]One letter amino acid code; conservative substitutions are underlined
[b]Position in gene product of first amino acid
[c]FAD6 = Plastid delta-12
[d]FAD3 = Microsomal delta-15
[e]FAD7 = Plastid delta-15

Example 2

Gene-Specific Oligonucleotide Markers for the Mutant and Wild Type Delta-12 Fatty Acid Desaturase Genes The D form of IMC129 fad2 gene contains a G to A transversion at nucleotide 316 from the translation initiation codon. Two short oligonucleotide upstream (5') primers, based on the single base change (G to A) between the D form of the IMC129 and wild type FAD2 genes, were designed. The sequences of the upstream (5') primers are as follows:

```
5' gene-specific primer for wild type FAD2-D:
5'-GTCTGGGTCATAGCCCACG-3'    (SEQ ID NO: 13); and 5' gene specific primer for IMC129 fad2-d:
5'-GTCTGGGTCATAGCCCACA-3'    (SEQ ID NO: 14).
```

A common downstream (3') primer (SEQ ID NO:10) specific for the D form of the FAD2 gene was used for both IMC129 and wild type FAD2 genes. These gene-specific primers were used in a DNA based PCR diagnostic assay to genotype plants carrying the mutant and/or wild type FAD2 genes.

Genomic DNA was isolated from leaf tissue of IMC129 and Westar plants, and used as PCR templates. The PCR amplification assays were carried out by using a gene amplification kit (Perkin Elmer). The PCR conditions are as follows: denaturing temperature, 95° C. for 1 min; annealing temperature, 52° C. for 1 min; amplification temperature 72° C. for 1 min. Total 20 PCR cycles were extended. Under these conditions primers SEQ ID NO:13 and SEQ ID NO:14 only amplified wild type FAD2-D and IMC 129 mutant fad2-d gene fragments, respectively.

The specificity of the gene-specific primers could be further improved by shortening the length of the primers and by replacing the base C with a T at the second position from the 3' end of the oligonucleotide PCR primer for FAD2-D (SEQ ID NO:13). The sequences of the modified upstream (5') oligonucleotide PCR primers are as follows:

```
5' modified gene-specific primer for wild
type FAD2-D:
5'-CTGGGTCATAGCCCATG-3'    (SEQ ID NO: 15); and 5' modified gene-specific primer for IMC129
fad2-d:
5'-CTGGGTCATAGCCCACA-3'    (SEQ ID NO: 16).
```

The same common downstream (3') oligonucleotide primer (SEQ ID NO:10) was used for amplifying FAD2-D and fad2-d. With the modified primers, the genotype for FAD2-D and fad2-d could be consistently distinguished after extended 30 cycle of PCR amplification. Therefore, the DNA based PCR assay provided a simple and reliable method of genotypping *B. Napus* germplasms containing mutant and/or wild type FAD2 genes.

Example 3

Constructs for Dominant Negative Suppression of Delta-12 Fatty Acid Desaturase

The vector pZS212 was used to construct plasmids for dominant negative suppression experiments. One construct was prepared by inserting the full-length mutant D gene coding sequence (nucleotides 1 to 1155 of SEQ ID NO:3) in sense orientation between the phaseolin promoter and phaseolin 3' poly A region of plasmid pCW108. The pCW108 vector contains the bean phaseolin promoter and 3' untranslated region and was derived from the commercially available pUC18 plasmid (Gibco-BRL) via plasmids AS3 and pCW104. Plasmid AS3 contains 495 base pairs of the bean (*Phaseolus vulgaris*) phaseolin (7S seed storage protein) promoter starting with 5'-TGGTCTTTTGGT-3' (SEQ ID NO:56) followed by the entire 1175 base pairs of the 3' untranslated region of the same gene (see sequence descriptions in Doyle et al., (1986) *J. Biol. Chem.* 261:9228–9238 and Slightom et al., (1983) *Proc. Natl. Acad. Sci. USA,* 80:1897–1901. Further sequence description may be found in WO 9113993) cloned into the Hind III site of pUC18. The 5 additional cloning sites of the pUC18 multiple cloning region (Eco RI, Sph I, Pst I and Sal I) were removed by digesting with Eco RI and Sal I, filling in the ends with Klenow and religating to yield the plasmid pCW104. A new multiple cloning site was created between the 495 bp of the 5' phaseolin and the 1175 bp of the 3' phaseolin by inserting a dimer of complementary synthetic oligonucleotides consisting of the coding sequence for a Nco I site (5'-CCATGG-3') followed by three filler bases (5'-TAG-3'), the coding sequence for a Sma I site (5' CCCGGG-3'), the last three bases of a Kpn I site (5'-TAC-3'), a cytosine and the coding sequence for an Xba I site (5'-TCTAGA-3') to create the plasmid pCW108. This plasmid contains unique Nco I, Sma I, Kpn I and Xba I sites directly behind the phaseolin promoter.

Figure 1:
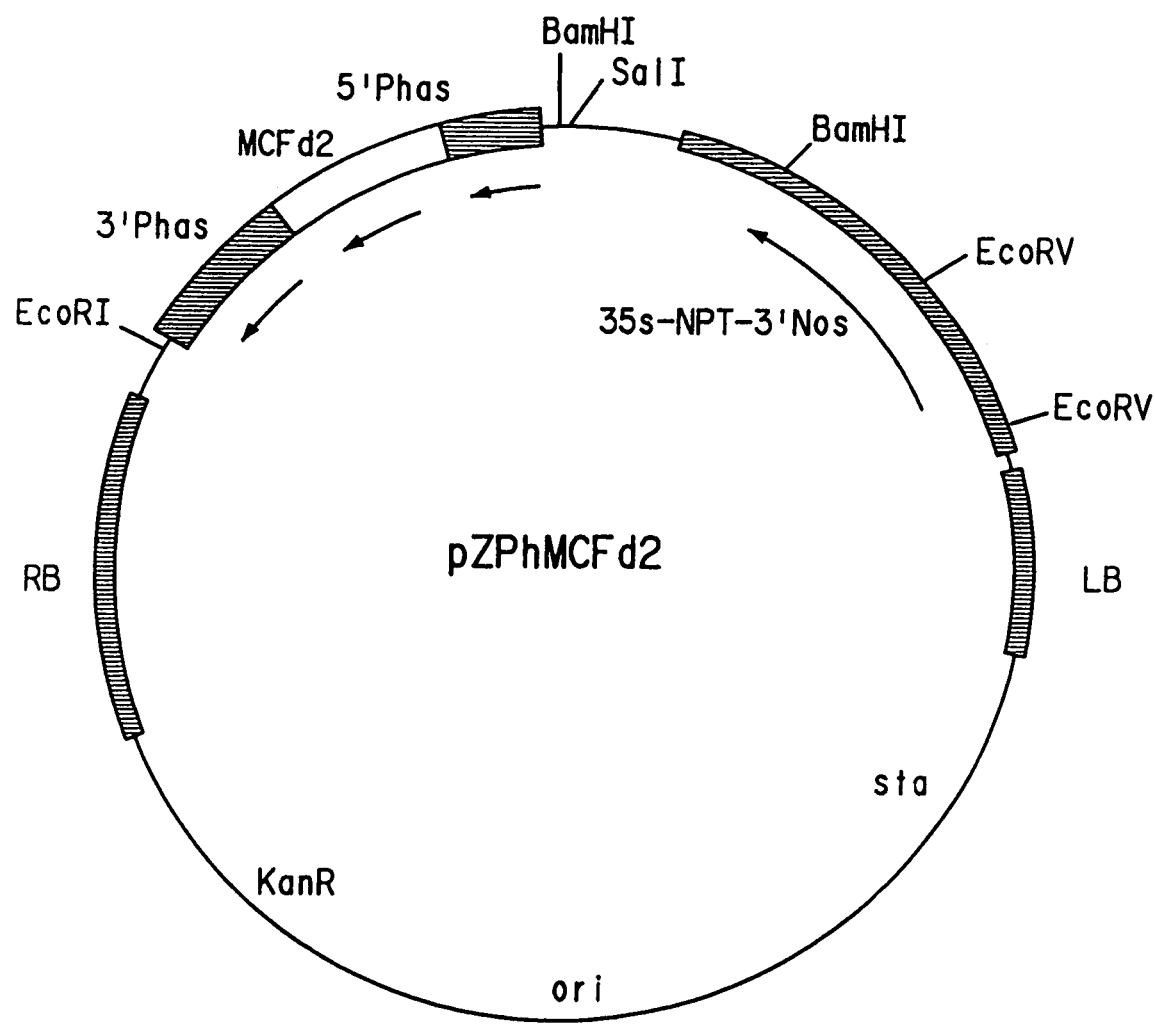
FIG. 1 is a schematic drawing of plasmid pZPhMcFd2, showing restriction sites and relative position and orientation of the bean phaseolin promoter (5' Phas), the IMC129 mutant microsomal delta-12 fatty acid desaturase D form coding sequence (MCFd2) and the bean phaseolin 3' untranslated region (3' Phas).

The resulting 5'-phaseolin promoter-mutant fad2-phaseolin poly A-3' construct was excised and cloned between the EcoRI/SalI sites of pZS212, resulting in the plasmid designated pZPhMCFd2 (FIG. 1). pZS212 is based on a vector which contains: (1) the chimeric gene nopaline synthase/neomycin phosphotransferase as a selectable marker for transformed plant cells (Brevan et al. (1984) *Nature* 304: 184–186), (2) the left and right borders of the T-DNA of the Ti plasmid (Brevan et al. (1984) *Nucl. Acids Res.* 12:8711–8720), (3) the *E. coli* lacZ α-complementing segment (Vieria and Messing (1982) *Gene* 19:259–267) with unique restriction endonuclease sites for Eco RI, Kpn I, Bam HI, and Sal I, (4) the bacterial replication origin from the *Pseudomonas* plasmid pVS1 (Itoh et al. (1984) *Plasmid* 11:206–220), and (5) the bacterial neomycin phosphotransferase gene from Tn5 (Berg et al. (1975) *Proc. Natnl. Acad. Sci. U.S.A.* 72:3628–3632) as a selectable marker for transformed *A. tumefaciens*. The nopaline synthase promoter in the plant selectable marker was replaced by the 35S promoter (Odell et al. (1985) *Nature,* 313:810–813) by a standard restriction endonuclease digestion and ligation strategy.

A second plasmid was constructed by inserting the full-length wild type canola D gene coding sequence (nucleotides 130 to 1281 of SEQ ID NO:1) into the NotI site of the canola napin promoter expression vector pIMC401 which contains a 2.2 kb napin expression cassette.

Figure 2:
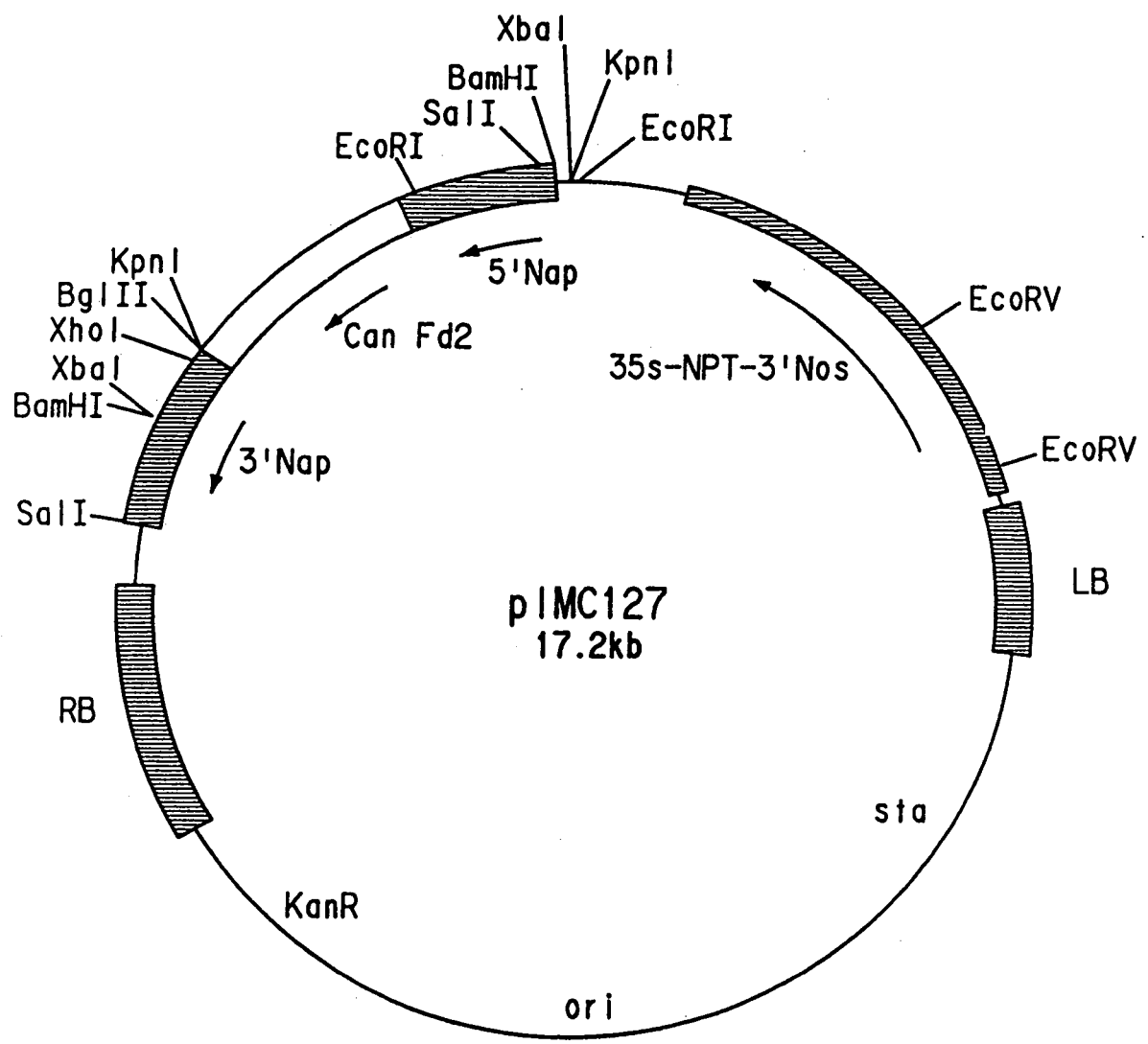
FIG. 2 is a schematic drawing of plasmid pIMC127, showing restriction sites and the relative positions and orientation of the napin promoter (5' nap), the wild-type microsomal delta-12 fatty acid desaturase D form coding sequence (CanFd2) and the napin 3' untranslated region (3' Nap).

The canola napin promoter expression cassette in pIMC401 was constructed as follows: ten oligonucleotide primers were synthesized based upon the nucleotide sequence of napin lambda clone CGN1–2 published in European Patent Application EP 255378). The oligonucleotide sequences were:

BR42 and BR43 corresponding to bases 1132 to 1156 (BR42) and the complement of bases 2248 to 2271 (BR43) of the sequence listed in FIG. 2 of EP 255378.

BR45 and BR46 corresponding to bases 1150 to 1170 (BR46) and the complement of bases 2120 to 2155 (BR45) of the sequence listed in FIG. 2 of EP 255378. In addition BR46 had bases corresponding to a Sal I site (5'-GTCGAC-3') and a few additional bases (5'-TCAGGCCT-3') at its 5' end and BR45 had bases corresponding to a Bgl II site (5'-AGATCT-3') and two (5'-CT-3') additional bases at the 5' end of the primer, BR47 and BR48 corresponding to bases 2705 to 2723 (BR47) and bases 2643 to 2666 (BR48) of the sequence listed in FIG. 2 of EP 255378. In addition BR47 had two (5'-CT-3') additional bases at the 5' end of the primer followed by bases corresponding to a Bgl II site (5'-AGATCT-3') followed by a few additional bases (5'-TCAGGCCT-3'), BR49 and BR50 corresponding to the complement of bases 3877 to 3897 (BR49) and the complement of bases 3985 to 3919 (BR50) of the sequence listed in FIG. 2 of EP 255378. In addition BR49 had bases corresponding to a Sal I site (5'-GTCGAC-3') and a few additional bases (5'-TCAGGCCT-3') at its 5' end, BR57 and BR58 corresponding to the complement of bases 3875 to 3888 (BR57) and bases 2700 to 2714 (BR58) of the sequence listed in FIG. 2 of EP 255378. In addition the 5' end of BR57 had some extra bases (5'-CCATGG-3') followed by bases corresponding to a Sac I site (5'-GAGCTC-3') followed by more additional bases (5'-GTCGACGAGG-3') (SEQ ID NO:57. The 5' end of BR58 had additional bases (5'-GAGCTC-3') followed by bases corresponding to a Nco I site (5'-CCATGG-3') followed by additional bases (5'-AGATCTGGTACC-3') (SEQ ID NO:58).

BR61 and BR62 corresponding to bases 1846 to 1865 (BR61) and bases 2094 to 2114 (BR62) of the sequence listed in FIG. 2 of EP 255378. In addition the 5' end of BR 62 had additional bases (5'-GACA-3') followed by bases corresponding to a Bgl II site (5'-AGATCT-3') followed by a few additional bases (5'-GCGGCCGC-3').

Genomic DNA from the canola variety 'Hyola401' (Zeneca Seeds) was used as a template for PCR amplification of the napin promoter and napin terminator regions. The promoter was first amplified using primers BR42 and BR43, and reamplified using primers BR45 and BR46. Plasmid pIMC01 was derived by digestion of the 1.0 kb promoter PCR product with SalI/BglII and ligation into SalI/BamHI digested pBluescript SK⁺(Stratagene). The napin terminator region was amplified using primers BR48 and BR50, and reamplified using primers BR47 and BR49. Plasmid pIMC06 was derived by digestion of the 1.2 kb terminator PCR product with SalI/BglII and ligation into SalI/BglII digested pSP72 (Promega). Using pIMC06 as a template, the terminator region was reamplified by PCR using primer BR57 and primer BR58. Plasmid pIMC101 containing both the napin promoter and terminator was generated by digestion of the PCR product with SacI/NcoI and ligation into SacI/NcoI digested pIMC01. Plasmid PIMC101 contains a 2.2 kb napin expression cassette including complete napin 5' and 3' non-translated sequences and an introduced NcoI site at the translation start ATG. Primer BR61 and primer BR62 were used to PCR amplify an ~270 bp fragment from the 3' end of the napin promoter. Plasmid pIMC401 was obtained by digestion of the resultant PCR product with EcoRI/BglII and ligation into EcoRI/BglII digested pIMC101. Plasmid pIMC401 contains a 2.2 kb napin expression cassette lacking the napin 5' non-translated sequence and includes a NotI site at the transcription start.

The fragment containing the 5'-napin-fad2D-napin poly A-3' cassette was then inserted into the SalI site of pZS212, and the resulting 17.2 Kb plasmid was termed pIMC127 (FIG. 2).

A third plasmid, pIMC135, was constructed in a manner similar to that described above for pIMC127. Plasmid pIMC135 contains a 5' cruciferin promoter fragment operably linked in sense orientation to the full-length wild-type coding sequence of SEQ ID NO:1, followed by a cruciferin 3' poly A fragment.

A fourth plasmid, pIMC140 was constructed in a manner similar to that described above. Plasmid pIMC140 contains a 5' napin promoter fragment operably linked in sense orientation to the full-length mutant Q508 F gene coding sequence (SEQ ID NO:7), followed by a 3' napin poly A fragment.

Example 4

Fatty Acid Profiles in Dominant Negative Suppression Plants

The plasmids pZPhMCFd2, pIMC127, pIMC135 and pIMC140 were transferred by a freeze/thaw method (Holsters et al. (1978) *Mol Gen Genet* 163:181–187) to the *Agrobacterium* strain LBA4404/pAL4404 (Hockema et al. (1983), *Nature* 303:179–180).

*Brassica napus* cultivar "Westar" was transformed by co-cultivation of seedling pieces with disarmed *Agrobacterium tumefaciens* strain LBA4404 carrying the appropriate binary vector.

*B. napus* seeds were sterilized by stirring in 10% Chlorox, 0.1% SDS for thirty min, and then rinsed thoroughly with sterile distilled water. The seeds were germinated on sterile medium containing 30 mM $CaCl_2$ and 1.5% agar, and grown for six days in the dark at 24° C.

Liquid cultures of *Agrobacterium* for plant transformation were grown overnight at 28° C. in Minimal A medium containing 100 mg/L kanamycin.

Minimal A Bacterial Growth Medium
  Dissolve in distilled water:
  10.5 grams potassium phosphate, dibasic
  4.5 grams potassium phosphate, monobasic
  1.0 gram ammonium sulfate
  0.5 gram sodium citrate, dihydrate
  Make up to 979 mL with distilled water
  Autoclave
  Add 20 mL filter-sterilized 10% sucrose
  Add 1 mL filter-sterilized 1 M $MgSO_4$ The bacterial cells were pelleted by centrifugation and resuspended at a concentration of $10^8$ cells/mL in liquid Murashige and Skoog Minimal Organic medium (GIBCO; Cat. No. 510–3118) containing 100 μM acetosyringone.

*B. napus* seedling hypocotyls were cut into 5 mm segments which were immediately placed into the bacterial suspension. After 30 min, the hypocotyl pieces were removed from the bacterial suspension and placed onto BC-35 callus medium containing 100 μM acetosyringone.

| *Brassica* Callus Medium BC-35 |
| --- |
| Per liter: |
| Murashige and Skoog Minimal Organic Medium (MS salts, 100 mg/L i-inositol, 0.4 mg/L thiamine; GIBCO #510-3118) |
| 30 grams sucrose |
| 18 grams mannitol |
| 0.5 mg/L 2,4-D |
| 0.3 mg/L kinetin |
| 0.6% agarose |
| pH 5.8 |

The plant tissue and *Agrobacteria* were co-cultivated for three days at 24° C. in dim light.

The co-cultivation was terminated by transferring the hypocotyl pieces to BC-35 callus medium containing 200 mg/L carbenicillin to kill the *Agrobacteria*, and 25 mg/L kanamycin to select for transformed plant cell growth. The seedling pieces were incubated on this medium for three weeks at 28° C. under continuous light.

After four weeks, the segments were transferred to BS-48 regeneration medium containing 200 mg/L carbenicillin and 25 mg/L kanamycin.

| *Brassica* Regeneration Medium BS-48 |
| --- |
| Murashige and Skoog Minimal Organic Medium |
| Gamborg B5 Vitamins (SIGMA #1019) |
| 10 grams glucose |
| 250 mg xylose |
| 600 mg MES |
| 0.4% agarose |
| pH 5.7 |
| Filter-sterilize and add after autoclaving: |
| 2.0 mg/L zeatin |
| 0.1 mg/L IAA |

Plant tissue was subcultured every two weeks onto fresh selective regeneration medium, under the same culture conditions described for the callus medium. Putatively transformed calli grew rapidly on regeneration medium; as calli reached a diameter of about 2 mm, they were removed from the hypocotyl pieces and placed on the same medium lacking kanamycin.

Shoots began to appear within several weeks after transfer to BS-48 regeneration medium. As soon as the shoots form d discernable stems, they were xcised from the calli, transferred to MSV-1A elongation medium, and moved to a 16:8 h photoperiod at 24° C.

*Brassica* Shoot Elongation Medium MSV-1A
  Murashige and Skoog Minimal Organic M dium
  Gamborg B5 Vitamins
  10 grams sucrose
  0.6% agarose
  pH 5.8

Once shoots had elongated several internodes, they were cut above the agar surface and the cut ends were dipped in Rootone. Treated shoots were planted directly into wet Metro-Mix 350 soilless potting medium. The pots were covered with plastic bags which were removed when the plants were clearly growing—after about ten days.

Plants were grown under a 16:8 h photoperiod, with a daytime temperature of 23° C. and a nightime temperature of 17° C. When the primary flowering stem began to elongate, it was covered with a mesh pollen-containment bag to prevent outcrossing. Self-pollination was facilitated by shaking the plants several times each day.

Tranagenic progeny plants containing pZPhMCFd2 were designated as the WS201 series. Plants transformed with pIMC127 were designated as the WS127 series. Plants transformed with pIMC135 were designated as the WS135 series. Plants transformed with pIMC140 were designated as the WS140 series. Seeds were obtained by selfing the T1 plants. Fatty acid profiles of the T2 seeds were determined as described in WO 93/11245. The results are shown in Tables 3 and 4 and FIGS. 3 and 4.

TABLE 3

T2 Seeds having Decreased
C18:2 (WS201[1] Transformants)[2].

| Line No. | Plant Series | Fatty Acid Composition (%) | | | | |
|---|---|---|---|---|---|---|
| | | C16:0 | C18:0 | C18:1 | C18:2 | C18:3 |
| T300236 | WS201 | 4.1 | 3.2 | 72.5 | 10.6 | 6.5 |
| T300238 | WS201 | 3.9 | 2.7 | 74.4 | 9.2 | 6.6 |
| T300390 | WS201 | 4.2 | 2.5 | 75.4 | 9.3 | 5.4 |
| T300273 | WS201 | 3.9 | 2.8 | 77.4 | 7.5 | 5.3 |
| T300400 | WS201 | 3.9 | 2.5 | 78.6 | 6.6 | 5.3 |
| T300354 | WS201 | 4.0 | 2.7 | 78.6 | 6.4 | 4.51 |

[1]WS201: phaseolin promoter/IMC129 mutant, sense orientation.
[2]Population of 168 selfed individuals from greenhouse.

Figure 3:
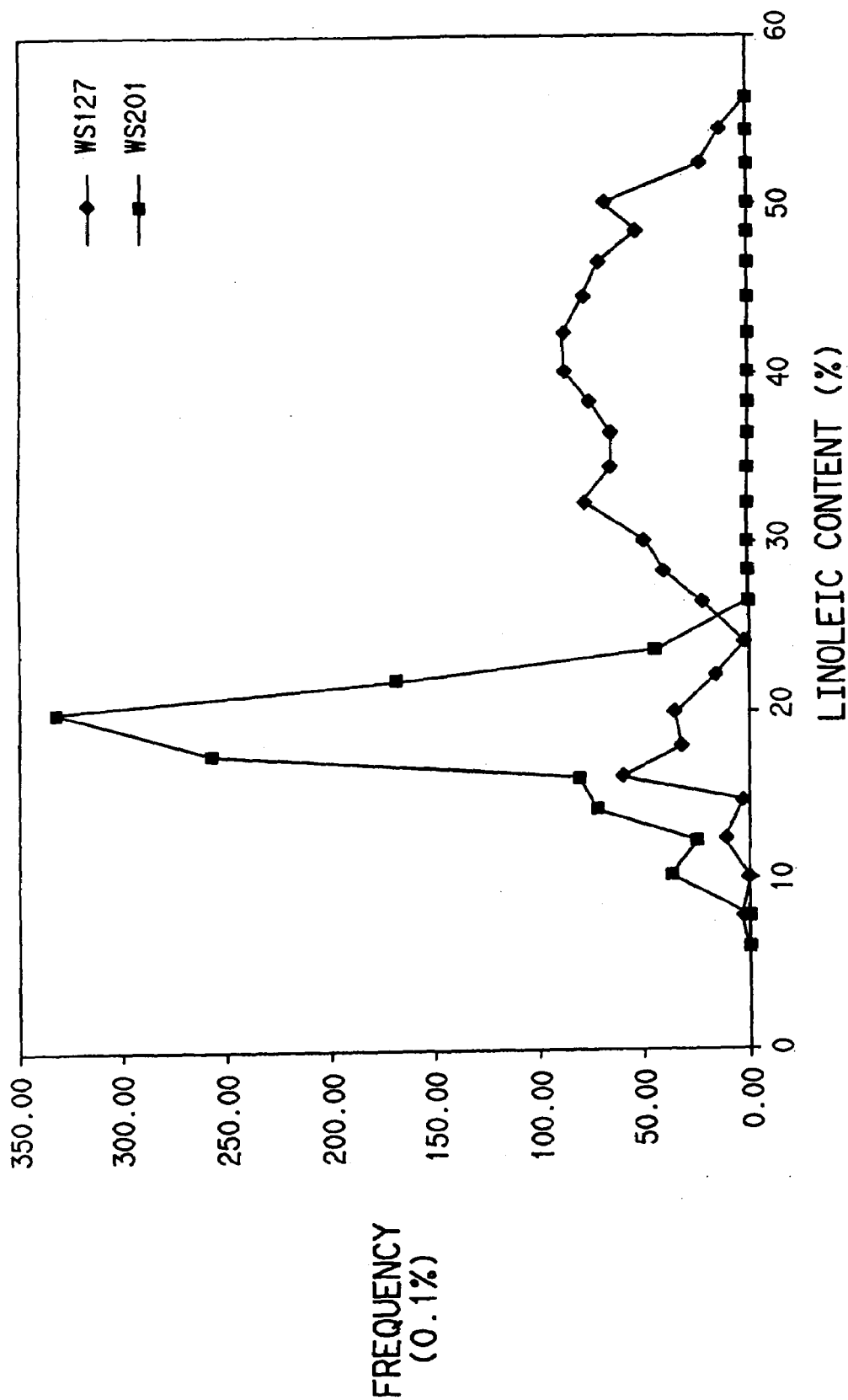

As shown in FIG. 3, a large proportion of the control WS127 plants have elevated levels of linoleic acid. This result is expected, since the delta-12 desaturase gene dosage is higher due to the extra copy of the wild-type delta-12 desaturase gene. A small proportion of WS127 plants show lower levels of linoleic acid, due to cosuppression.

In contrast, no WS201 plants had elevated levels of linoleic acid. This result confirms that the mutant delta-12 desaturase D form gene in WS201 plants is non-functional. Furthermore, a higher proportion of WS201 plants have decreased C18:2 (5–14%) compared to the proportion of WS127 control plants having decreased C18:2. The proportion of WS201 plants having decreased C18:2 is about 25-fold higher than the proportion of WS127 plants having decreased C18:2. The surprising inhibition of endogenous delta-12 desaturase activity by a mutant delta-12 gene product has been termed dominant negative suppression.

The fatty acid composition of seeds produced by representative dominant negative suppression T2 WS201 plants is shown in Table 3. The plants show an altered fatty acid composition, including decreased C18:2, increased C18:1, and decreased saturates.

A T2 generation plant is not homozygous for the introduced gene. Consequently, T3 and subsequent generations that are homozygous for the mutant delta-12 desaturase gene will have even lower levels of linoleic acid, from about 1% to about 10%, preferably from about 1% to about 6%. Levels of oleic acid in homozygous lines will be from 75% to about 88%, preferably from about 80% to about 88%.

The results observed with WS140 plants (containing a mutant Q508 F form delta-12 desaturase gene) are shown in FIG. 4. None of the WS140 plants have elevated C18:2 levels, similar to the results obtained with WS201 transgenic plants. As expected, a large proportion of the control WS135 plants have elevated C18:2 levels. The proportion of WS140 and WS135 plants having decreased C18:2 levels is similar, indicating that expression of this particular mutant delta-12 desaturase gene product does not inhibit endogenous wild-type delta-12 desaturase gene product to an extent greater than that expected from cosuppression. The fatty acid composition of seeds produced by a representative T2 WS140 plant with decreased C18:2 levels is shown in Table 4.

TABLE 4

T2 Seed Having Decreased C18:2 (WS140[1] Transformants)[2].

| Line No. | Vector | Fatty Acid Composition (%) | | | | |
|---|---|---|---|---|---|---|
| | | C16:0 | C18:0 | C18:1 | C18:2 | C18:3 |
| T300435 | pIMC140 | 3.8 | 3.5 | 73.7 | 9.7 | 6.11 |

[1]WS140: napin promoter/Q508 fad2 F mutation, sense orientation
[2]Population of 61 selfed individuals from greenhouse

---

The invention claimed is:

1. A method for increasing the oleic acid content in plant seeds, comprising the steps of:
   a) introducing a recombinant nucleic acid construct into a plant, said construct comprising at least one seed-specific regulatory sequence operably linked in sense orientation to a full length delta-12 fatty acid desaturase coding sequence, wherein said sequence encodes a delta-12 fatty acid desaturase protein having a substitution of a Lys residue for Asp or Glu in an amino acid region selected from the group consisting of His-Glu-Cys-Gly-His (SEQ ID NO:53), His-Asp-Cys-Gly-His (SEQ ID NO;55), and His-Asp-Cys-Ala-His (SEQ ID NO:54),
   b) obtaining progeny from said plant, said progeny producing said seeds having an oleic acid content of from about 72.5% to about 78.6%.

2. A recombinant nucleic acid construct effective for increasing oleic acid content when expressed in seeds, said construct comprising at least one seed-specific regulatory sequence operably linked in sense orientation to a delta-12 fatty acid desaturase coding sequence encoding a delta-12 fatty acid desaturase gene product having at least one mutation which renders said desaturase gene product nonfunctional, said mutation being the substitution of a Lys residue for Asp in an amino acid region selected from the group consisting of His-Asp-Cys-Gly-His (SEQ ID NO:55) and His-Asp-Cys-Ala-His (SEQ ID NO:54).

3. The method of claim 1, wherein said substitution is in a His-Glu-Cys-Gly-His (SEQ ID NO:53) amino acid region.

4. The method of claim 1, wherein said plant is soybean.

5. The method of claim 1, wherein said plant is rapeseed.

6. The method of claim 1, wherein said plant is cotton.

7. The method of claim 1, wherein said plant is corn.

8. The method of claim 1, wherein said plant is safflower.

9. The method of claim 1, wherein said seed-specific regulatory sequence is a bean β-phaseolin promoter.

10. The method of claim 1, wherein said seed-specific regulatory sequence is an αsubunit of soybean β-conglycinin promoter.

11. The method of claim 1, wherein said seed-specific regulatory sequence is maize 18 kd oleosin promoter.

12. The method of claim 1, wherein said seed-specific regulatory sequence is maize 15 kd zein promoter.

13. The method of claim 1, wherein said seed-specific regulatory sequence is a *Brassica* napin promoter.

14. The method of claim 1, wherein said seeds have a linoleic acid content of about 6.4% to about 10.6%.

15. The method of claim 1, wherein said seeds have an α-linolenic acid content of about 4.5% to about 6.5%.

* * * * *

UNITED STATES PATENT AND TRADEMARK OFFICE
CERTIFICATE OF CORRECTION

PATENT NO.       : 7,109,392 B1
APPLICATION NO.  : 09/643579
DATED            : September 19, 2006
INVENTOR(S)      : Richard Broglie et al.

It is certified that error appears in the above-identified patent and that said Letters Patent is hereby corrected as shown below:

Column 61, line 36, please delete "NO;55" and insert --NO:55--therefor;

Column 62, line 36, please delete "αsubunit" and insert --α subunit--therefor.

Signed and Sealed this

Third Day of July, 2007

JON W. DUDAS
*Director of the United States Patent and Trademark Office*

SEQUENCE LISTING

<160> NUMBER OF SEQ ID NOS: 58

<210> SEQ ID NO 1
<211> LENGTH: 1464
<212> TYPE: DNA
<213> ORGANISM: Brassica napus
<220> FEATURE:
<221> NAME/KEY: CDS
<222> LOCATION: (130)..(1281)

<400> SEQUENCE: 1

```
ggcacgagct cgtgccgaat tcggcacgag aggagacaga gagagagttt gaggaggagc        60
ttcttcgtag ggttcatcgt tattaacgtt aaatcttcat ccccccctac gtcagccagc       120 tcaagaaac atg ggt gca ggt gga aga atg caa gtg tct cct ccc tcc           168
           Met Gly Ala Gly Gly Arg Met Gln Val Ser Pro Pro Ser
             1               5                  10 aaa aag tct gaa acc gac aac atc aag cgc gta ccc tgc gag aca ccg         216
Lys Lys Ser Glu Thr Asp Asn Ile Lys Arg Val Pro Cys Glu Thr Pro
     15                  20                  25 ccc ttc act gtc gga gaa ctc aag aaa gca atc cca ccg cac tgt ttc         264
Pro Phe Thr Val Gly Glu Leu Lys Lys Ala Ile Pro Pro His Cys Phe
 30                  35                  40                  45 aaa cgc tcg atc cct cgc tct ttc tcc tac ctc atc tgg gac atc atc         312
```

|     |     |     |     |     |     |     |     |     |     |     |     |     |     |     |     |     |
|---|---|---|---|---|---|---|---|---|---|---|---|---|---|---|---|---|
| Lys | Arg | Ser | Ile | Pro 50 | Arg | Ser | Phe | Ser | Tyr 55 | Leu | Ile | Trp | Asp | Ile 60 | Ile | |

```
ata gcc tcc tgc ttc tac tac gtc gcc acc act tac ttc cct ctc ctc      360
Ile Ala Ser Cys Phe Tyr Tyr Val Ala Thr Thr Tyr Phe Pro Leu Leu
             65                  70                  75 cct cac cct ctc tcc tac ttc gcc tgg cct ctc tac tgg gcc tgc cag      408
Pro His Pro Leu Ser Tyr Phe Ala Trp Pro Leu Tyr Trp Ala Cys Gln
         80                  85                  90 ggc tgc gtc cta acc ggc gtc tgg gtc ata gcc cac gag tgc ggc cac      456
Gly Cys Val Leu Thr Gly Val Trp Val Ile Ala His Glu Cys Gly His
     95                 100                 105 cac gcc ttc agc gac tac cag tgg ctg gac gac acc gtc ggc ctc atc      504
His Ala Phe Ser Asp Tyr Gln Trp Leu Asp Asp Thr Val Gly Leu Ile
110                 115                 120                 125 ttc cac tcc ttc ctc ctc gtc cct tac ttc tcc tgg aag tac agt cat      552
Phe His Ser Phe Leu Leu Val Pro Tyr Phe Ser Trp Lys Tyr Ser His
                130                 135                 140 cga cgc cac cat tcc aac act ggc tcc ctc gag aga gac gaa gtg ttt      600
Arg Arg His His Ser Asn Thr Gly Ser Leu Glu Arg Asp Glu Val Phe
                    145                 150                 155 gtc ccc aag aag aag tca gac atc aag tgg tac ggc aag tac ctc aac      648
Val Pro Lys Lys Lys Ser Asp Ile Lys Trp Tyr Gly Lys Tyr Leu Asn
            160                 165                 170 aac cct ttg gga cgc acc gtg atg tta acg gtt cag ttc act ctc ggc      696
Asn Pro Leu Gly Arg Thr Val Met Leu Thr Val Gln Phe Thr Leu Gly
        175                 180                 185 tgg cct ttg tac tta gcc ttc aac gtc tcg ggg aga cct tac gac ggc      744
Trp Pro Leu Tyr Leu Ala Phe Asn Val Ser Gly Arg Pro Tyr Asp Gly
190                 195                 200                 205 ggc ttc gct tgc cat ttc cac ccc aac gct ccc atc tac aac gac cgt      792
Gly Phe Ala Cys His Phe His Pro Asn Ala Pro Ile Tyr Asn Asp Arg
                210                 215                 220 gag cgt ctc cag ata tac atc tcc gac gct ggc atc ctc gcc gtc tgc      840
Glu Arg Leu Gln Ile Tyr Ile Ser Asp Ala Gly Ile Leu Ala Val Cys
                    225                 230                 235 tac ggt ctc tac cgc tac gct gct gtc caa gga gtt gcc tcg atg gtc      888
Tyr Gly Leu Tyr Arg Tyr Ala Ala Val Gln Gly Val Ala Ser Met Val
            240                 245                 250 tgc ttc tac gga gtt cct ctt ctg att gtc aac ggg ttc tta gtt ttg      936
Cys Phe Tyr Gly Val Pro Leu Leu Ile Val Asn Gly Phe Leu Val Leu
        255                 260                 265 atc act tac ttg cag cac acg cat cct tcc ctg cct cac tat gac tcg      984
Ile Thr Tyr Leu Gln His Thr His Pro Ser Leu Pro His Tyr Asp Ser
270                 275                 280                 285 tct gag tgg gat tgg ttg agg gga gct ttg gcc acc gtt gac aga gac     1032
Ser Glu Trp Asp Trp Leu Arg Gly Ala Leu Ala Thr Val Asp Arg Asp
                290                 295                 300 tac gga atc ttg aac aag gtc ttc cac aat atc acg gac acg cac gtg     1080
Tyr Gly Ile Leu Asn Lys Val Phe His Asn Ile Thr Asp Thr His Val
                    305                 310                 315 gcg cat cac ctg ttc tcg acc atg ccg cat tat cat gcg atg gaa gct     1128
Ala His His Leu Phe Ser Thr Met Pro His Tyr His Ala Met Glu Ala
            320                 325                 330 acg aag gcg ata aag ccg ata ctg gga gag tat tat cag ttc gat ggg     1176
Thr Lys Ala Ile Lys Pro Ile Leu Gly Glu Tyr Tyr Gln Phe Asp Gly
        335                 340                 345 acg ccg gtg gtt aag gcg atg tgg agg gag gcg aag gag tgt atc tat     1224
Thr Pro Val Val Lys Ala Met Trp Arg Glu Ala Lys Glu Cys Ile Tyr
350                 355                 360                 365
```

-continued

```
gtg gaa ccg gac agg caa ggt gag aag aaa ggt gtg ttc tgg tac aac      1272
Val Glu Pro Asp Arg Gln Gly Glu Lys Lys Gly Val Phe Trp Tyr Asn
                370                 375                 380 aat aag tta tgaagcaaag aagaaactga acctttctct tctatgattg              1321
Asn Lys Leu tctttgttta agaagctatg tttctgtttc aataatctta attatccatt ttgttgtgtt   1381
ttctgacatt ttggctaaaa ttatgtgatg ttggaagtta gtgtctaaaa aaaaaaaaa    1441 aaaaaaaaaa aaaaaaaaaa aaa                                            1464
```

<210> SEQ ID NO 2
<211> LENGTH: 384
<212> TYPE: PRT
<213> ORGANISM: Brassica napus

<400> SEQUENCE: 2

```
Met Gly Ala Gly Gly Arg Met Gln Val Ser Pro Ser Lys Lys Ser
  1               5                  10                  15

Glu Thr Asp Asn Ile Lys Arg Val Pro Cys Glu Thr Pro Pro Phe Thr
                 20                  25                  30

Val Gly Glu Leu Lys Lys Ala Ile Pro Pro His Cys Phe Lys Arg Ser
             35                  40                  45

Ile Pro Arg Ser Phe Ser Tyr Leu Ile Trp Asp Ile Ile Ala Ser
 50                  55                  60

Cys Phe Tyr Tyr Val Ala Thr Thr Tyr Phe Pro Leu Leu Pro His Pro
 65                  70                  75                  80

Leu Ser Tyr Phe Ala Trp Pro Leu Tyr Trp Ala Cys Gln Gly Cys Val
                 85                  90                  95

Leu Thr Gly Val Trp Val Ile Ala His Glu Cys Gly His His Ala Phe
            100                 105                 110

Ser Asp Tyr Gln Trp Leu Asp Asp Thr Val Gly Leu Ile Phe His Ser
            115                 120                 125

Phe Leu Leu Val Pro Tyr Phe Ser Trp Lys Tyr Ser His Arg Arg His
130                 135                 140

His Ser Asn Thr Gly Ser Leu Glu Arg Asp Glu Val Phe Val Pro Lys
145                 150                 155                 160

Lys Lys Ser Asp Ile Lys Trp Tyr Gly Lys Tyr Leu Asn Asn Pro Leu
                165                 170                 175

Gly Arg Thr Val Met Leu Thr Val Gln Phe Thr Leu Gly Trp Pro Leu
            180                 185                 190

Tyr Leu Ala Phe Asn Val Ser Gly Arg Pro Tyr Asp Gly Gly Phe Ala
            195                 200                 205

Cys His Phe His Pro Asn Ala Pro Ile Tyr Asn Asp Arg Glu Arg Leu
            210                 215                 220

Gln Ile Tyr Ile Ser Asp Ala Gly Ile Leu Ala Val Cys Tyr Gly Leu
225                 230                 235                 240

Tyr Arg Tyr Ala Ala Val Gln Gly Val Ala Ser Met Val Cys Phe Tyr
                245                 250                 255

Gly Val Pro Leu Leu Ile Val Asn Gly Phe Leu Val Leu Ile Thr Tyr
            260                 265                 270

Leu Gln His Thr His Pro Ser Leu Pro His Tyr Asp Ser Ser Glu Trp
            275                 280                 285

Asp Trp Leu Arg Gly Ala Leu Ala Thr Val Asp Arg Asp Tyr Gly Ile
            290                 295                 300

Leu Asn Lys Val Phe His Asn Ile Thr Asp Thr His Val Ala His His
```

-continued

```
                305                 310                 315                 320
Leu Phe Ser Thr Met Pro His Tyr His Ala Met Glu Ala Thr Lys Ala
                    325                 330                 335

Ile Lys Pro Ile Leu Gly Glu Tyr Tyr Gln Phe Asp Gly Thr Pro Val
                340                 345                 350

Val Lys Ala Met Trp Arg Glu Ala Lys Glu Cys Ile Tyr Val Glu Pro
            355                 360                 365

Asp Arg Gln Gly Glu Lys Lys Gly Val Phe Trp Tyr Asn Asn Lys Leu
        370                 375                 380
```

<210> SEQ ID NO 3
<211> LENGTH: 1155
<212> TYPE: DNA
<213> ORGANISM: Brassica napus
<220> FEATURE:
<221> NAME/KEY: CDS
<222> LOCATION: (1)..(1152)

<400> SEQUENCE: 3

```
atg ggt gca ggt gga aga atg caa gtg tct cct ccc tcc aaa aag tct      48
Met Gly Ala Gly Gly Arg Met Gln Val Ser Pro Pro Ser Lys Lys Ser
 1               5                  10                  15 gaa acc gac aac atc aag cgc gta ccc tgc gag aca ccg ccc ttc act      96
Glu Thr Asp Asn Ile Lys Arg Val Pro Cys Glu Thr Pro Pro Phe Thr
                20                  25                  30 gtc gga gaa ctc aag aaa gca atc cca ccg cac tgt ttc aaa cgc tcg     144
Val Gly Glu Leu Lys Lys Ala Ile Pro Pro His Cys Phe Lys Arg Ser
            35                  40                  45 atc cct cgc tct ttc tcc tac ctc atc tgg gac atc atc ata gcc tcc     192
Ile Pro Arg Ser Phe Ser Tyr Leu Ile Trp Asp Ile Ile Ile Ala Ser
        50                  55                  60 tgc ttc tac tac gtc gcc acc act tac ttc cct ctc ctc cct cac cct     240
Cys Phe Tyr Tyr Val Ala Thr Thr Tyr Phe Pro Leu Leu Pro His Pro
 65                  70                  75                  80 ctc tcc tac ttc gcc tgg cct ctc tac tgg gcc tgc cag ggc tgc gtc     288
Leu Ser Tyr Phe Ala Trp Pro Leu Tyr Trp Ala Cys Gln Gly Cys Val
                 85                  90                  95 cta acc ggc gtc tgg gtc ata gcc cac aag tgc ggc cac cac gcc ttc     336
Leu Thr Gly Val Trp Val Ile Ala His Lys Cys Gly His His Ala Phe
                100                 105                 110 agc gac tac cag tgg ctg gac gac acc gtc ggc ctc atc ttc cac tcc     384
Ser Asp Tyr Gln Trp Leu Asp Asp Thr Val Gly Leu Ile Phe His Ser
            115                 120                 125 ttc ctc ctc gtc cct tac ttc tcc tgg aag tac agt cat cga cgc cac     432
Phe Leu Leu Val Pro Tyr Phe Ser Trp Lys Tyr Ser His Arg Arg His
        130                 135                 140 cat tcc aac act ggc tcc ctc gag aga gac gaa gtg ttt gtc ccc aag     480
His Ser Asn Thr Gly Ser Leu Glu Arg Asp Glu Val Phe Val Pro Lys
145                 150                 155                 160 aag aag tca gac atc aag tgg tac ggc aag tac ctc aac aac cct ttg     528
Lys Lys Ser Asp Ile Lys Trp Tyr Gly Lys Tyr Leu Asn Asn Pro Leu
                165                 170                 175 gga cgc acc gtg atg tta acg gtt cag ttc act ctc ggc tgg cct ttg     576
Gly Arg Thr Val Met Leu Thr Val Gln Phe Thr Leu Gly Trp Pro Leu
            180                 185                 190 tac tta gcc ttc aac gtc tcg ggg aga cct tac gac ggc ggc ttc gct     624
Tyr Leu Ala Phe Asn Val Ser Gly Arg Pro Tyr Asp Gly Gly Phe Ala
        195                 200                 205 tgc cat ttc cac ccc aac gct ccc atc tac aac gac cgc gag cgt ctc     672
Cys His Phe His Pro Asn Ala Pro Ile Tyr Asn Asp Arg Glu Arg Leu
```

```
                 210                 215                 220
cag ata tac atc tcc gac gct ggc atc ctc gcc gtc tgc tac ggt ctc      720
Gln Ile Tyr Ile Ser Asp Ala Gly Ile Leu Ala Val Cys Tyr Gly Leu
225             230                 235                 240 tac cgc tac gct gct gtc caa gga gtt gcc tcg atg gtc tgc ttc tac      768
Tyr Arg Tyr Ala Ala Val Gln Gly Val Ala Ser Met Val Cys Phe Tyr
                245                 250                 255 gga gtt ccg ctt ctg att gtc aat ggg ttc tta gtt ttg atc act tac      816
Gly Val Pro Leu Leu Ile Val Asn Gly Phe Leu Val Leu Ile Thr Tyr
            260                 265                 270 ttg cag cac acg cat cct tcc ctg cct cac tac gat tcg tcc gag tgg      864
Leu Gln His Thr His Pro Ser Leu Pro His Tyr Asp Ser Ser Glu Trp
        275                 280                 285 gat tgg ttc agg gga gct ttg gcc acc gtt gac aga gac tac gga atc      912
Asp Trp Phe Arg Gly Ala Leu Ala Thr Val Asp Arg Asp Tyr Gly Ile
290                 295                 300 ttg aac aag gtc ttc cac aat atc acg gac acg cac gtg gcg cat cac      960
Leu Asn Lys Val Phe His Asn Ile Thr Asp Thr His Val Ala His His
305                 310                 315                 320 ctg ttc tcc acc atg ccg cat tat cat gcg atg gaa gct acc aag gcg     1008
Leu Phe Ser Thr Met Pro His Tyr His Ala Met Glu Ala Thr Lys Ala
                325                 330                 335 ata aag ccg ata ctg gga gag tat tat cag ttc gat ggg acg ccg gtg     1056
Ile Lys Pro Ile Leu Gly Glu Tyr Tyr Gln Phe Asp Gly Thr Pro Val
            340                 345                 350 gtt aag gcg atg tgg agg gag gcg aag gag tgt atc tat gtg gaa ccg     1104
Val Lys Ala Met Trp Arg Glu Ala Lys Glu Cys Ile Tyr Val Glu Pro
        355                 360                 365 gac agg caa ggt gag aag aaa ggt gtg ttc tgg tac aac aat aag tta t   1153
Asp Arg Gln Gly Glu Lys Lys Gly Val Phe Trp Tyr Asn Asn Lys Leu
370                 375                 380 ga                                                                   1155

<210> SEQ ID NO 4
<211> LENGTH: 384
<212> TYPE: PRT
<213> ORGANISM: Brassica napus

<400> SEQUENCE: 4

Met Gly Ala Gly Gly Arg Met Gln Val Ser Pro Ser Lys Lys Ser
  1               5                  10                  15

Glu Thr Asp Asn Ile Lys Arg Val Pro Cys Glu Thr Pro Pro Phe Thr
                 20                  25                  30

Val Gly Glu Leu Lys Lys Ala Ile Pro Pro His Cys Phe Lys Arg Ser
             35                  40                  45

Ile Pro Arg Ser Phe Ser Tyr Leu Ile Trp Asp Ile Ile Ala Ser
         50                  55                  60

Cys Phe Tyr Tyr Val Ala Thr Thr Tyr Phe Pro Leu Leu Pro His Pro
 65                  70                  75                  80

Leu Ser Tyr Phe Ala Trp Pro Leu Tyr Trp Ala Cys Gln Gly Cys Val
                 85                  90                  95

Leu Thr Gly Val Trp Val Ile Ala His Lys Cys Gly His His Ala Phe
            100                 105                 110

Ser Asp Tyr Gln Trp Leu Asp Asp Thr Val Gly Leu Ile Phe His Ser
        115                 120                 125

Phe Leu Leu Val Pro Tyr Phe Ser Trp Lys Tyr Ser His Arg Arg His
    130                 135                 140
```

-continued

```
His Ser Asn Thr Gly Ser Leu Glu Arg Asp Glu Val Phe Val Pro Lys
145                 150                 155                 160

Lys Lys Ser Asp Ile Lys Trp Tyr Gly Lys Tyr Leu Asn Asn Pro Leu
                165                 170                 175

Gly Arg Thr Val Met Leu Thr Val Gln Phe Thr Leu Gly Trp Pro Leu
            180                 185                 190

Tyr Leu Ala Phe Asn Val Ser Gly Arg Pro Tyr Asp Gly Gly Phe Ala
        195                 200                 205

Cys His Phe His Pro Asn Ala Pro Ile Tyr Asn Asp Arg Glu Arg Leu
    210                 215                 220

Gln Ile Tyr Ile Ser Asp Ala Gly Ile Leu Ala Val Cys Tyr Gly Leu
225                 230                 235                 240

Tyr Arg Tyr Ala Ala Val Gln Gly Val Ala Ser Met Val Cys Phe Tyr
                245                 250                 255

Gly Val Pro Leu Leu Ile Val Asn Gly Phe Leu Val Leu Ile Thr Tyr
            260                 265                 270

Leu Gln His Thr His Pro Ser Leu Pro His Tyr Asp Ser Ser Glu Trp
        275                 280                 285

Asp Trp Phe Arg Gly Ala Leu Ala Thr Val Asp Arg Asp Tyr Gly Ile
    290                 295                 300

Leu Asn Lys Val Phe His Asn Ile Thr Asp Thr His Val Ala His His
305                 310                 315                 320

Leu Phe Ser Thr Met Pro His Tyr His Ala Met Glu Ala Thr Lys Ala
                325                 330                 335

Ile Lys Pro Ile Leu Gly Glu Tyr Tyr Gln Phe Asp Gly Thr Pro Val
            340                 345                 350

Val Lys Ala Met Trp Arg Glu Ala Lys Glu Cys Ile Tyr Val Glu Pro
        355                 360                 365

Asp Arg Gln Gly Glu Lys Lys Gly Val Phe Trp Tyr Asn Asn Lys Leu
    370                 375                 380
```

<210> SEQ ID NO 5
<211> LENGTH: 1155
<212> TYPE: DNA
<213> ORGANISM: Brassica napus
<220> FEATURE:
<221> NAME/KEY: CDS
<222> LOCATION: (1)..(1152)

<400> SEQUENCE: 5

```
atg ggt gca ggt gga aga atg caa gtg tct cct ccc tcc aag aag tct      48
Met Gly Ala Gly Gly Arg Met Gln Val Ser Pro Pro Ser Lys Lys Ser
 1               5                  10                  15 gaa acc gac acc atc aag cgc gta ccc tgc gag aca ccg ccc ttc act      96
Glu Thr Asp Thr Ile Lys Arg Val Pro Cys Glu Thr Pro Pro Phe Thr
                20                  25                  30 gtc gga gaa ctc aag aaa gca atc cca ccg cac tgt ttc aaa cgc tcg     144
Val Gly Glu Leu Lys Lys Ala Ile Pro Pro His Cys Phe Lys Arg Ser
            35                  40                  45 atc cct cgc tct ttc tcc tac ctc atc tgg gac atc ata gcc tcc         192
Ile Pro Arg Ser Phe Ser Tyr Leu Ile Trp Asp Ile Ile Ala Ser
        50                  55                  60 tgc ttc tac tac gtc gcc acc act tac ttc cct ctc ctc cct cac cct     240
Cys Phe Tyr Tyr Val Ala Thr Thr Tyr Phe Pro Leu Leu Pro His Pro
 65                  70                  75                  80 ctc tcc tac ttc gcc tgg cct ctc tac tgg gcc tgc caa ggg tgc gtc     288
Leu Ser Tyr Phe Ala Trp Pro Leu Tyr Trp Ala Cys Gln Gly Cys Val
                85                  90                  95
```

```
cta acc ggc gtc tgg gtc ata gcc cac gag tgc ggc cac cac gcc ttc      336
Leu Thr Gly Val Trp Val Ile Ala His Glu Cys Gly His His Ala Phe
        100                 105                 110 agc gac tac cag tgg ctt gac gac acc gtc ggt ctc atc ttc cac tcc      384
Ser Asp Tyr Gln Trp Leu Asp Asp Thr Val Gly Leu Ile Phe His Ser
            115                 120                 125 ttc ctc ctc gtc cct tac ttc tcc tgg aag tac agt cat cgc agc cac      432
Phe Leu Leu Val Pro Tyr Phe Ser Trp Lys Tyr Ser His Arg Ser His
    130                 135                 140 cat tcc aac act ggc tcc ctc gag aga gac gaa gtg ttt gtc ccc aag      480
His Ser Asn Thr Gly Ser Leu Glu Arg Asp Glu Val Phe Val Pro Lys
145                 150                 155                 160 aag aag tca gac atc aag tgg tac ggc aag tac ctc aac aac cct ttg      528
Lys Lys Ser Asp Ile Lys Trp Tyr Gly Lys Tyr Leu Asn Asn Pro Leu
                165                 170                 175 gga cgc acc gtg atg tta acg gtt cag ttc act ctc ggc tgg ccg ttg      576
Gly Arg Thr Val Met Leu Thr Val Gln Phe Thr Leu Gly Trp Pro Leu
            180                 185                 190 tac tta gcc ttc aac gtc tcg gga aga cct tac gac ggc ggc ttc cgt      624
Tyr Leu Ala Phe Asn Val Ser Gly Arg Pro Tyr Asp Gly Gly Phe Arg
        195                 200                 205 tgc cat ttc cac ccc aac gct ccc atc tac aac gac cgc gag cgt ctc      672
Cys His Phe His Pro Asn Ala Pro Ile Tyr Asn Asp Arg Glu Arg Leu
    210                 215                 220 cag ata tac atc tcc gac gct ggc atc ctc gcc gtc tgc tac ggt ctc      720
Gln Ile Tyr Ile Ser Asp Ala Gly Ile Leu Ala Val Cys Tyr Gly Leu
225                 230                 235                 240 ttc cgt tac gcc gcc ggc cag gga gtg gcc tcg atg gtc tgc ttc tac      768
Phe Arg Tyr Ala Ala Gly Gln Gly Val Ala Ser Met Val Cys Phe Tyr
                245                 250                 255 gga gtc ccg ctt ctg att gtc aat ggt ttc ctc gtg ttg atc act tac      816
Gly Val Pro Leu Leu Ile Val Asn Gly Phe Leu Val Leu Ile Thr Tyr
            260                 265                 270 ttg cag cac acg cat cct tcc ctg cct cac tac gat tcg tcc gag tgg      864
Leu Gln His Thr His Pro Ser Leu Pro His Tyr Asp Ser Ser Glu Trp
        275                 280                 285 gat tgg ttc agg gga gct ttg gct acc gtt gac aga gac tac gga atc      912
Asp Trp Phe Arg Gly Ala Leu Ala Thr Val Asp Arg Asp Tyr Gly Ile
    290                 295                 300 ttg aac aag gtc ttc cac aat att acc gac acg cac gtc gcg cat cat      960
Leu Asn Lys Val Phe His Asn Ile Thr Asp Thr His Val Ala His His
305                 310                 315                 320 ccg ttc tcc acg atg ccg cat tat cac gcg atg gaa gct acc aag gcg     1008
Pro Phe Ser Thr Met Pro His Tyr His Ala Met Glu Ala Thr Lys Ala
                325                 330                 335 ata aag ccg ata ctg gga gag tat tat cag ttc gat ggg acg ccg gtg     1056
Ile Lys Pro Ile Leu Gly Glu Tyr Tyr Gln Phe Asp Gly Thr Pro Val
            340                 345                 350 gtt aag gcg atg tgg agg gag gcg aag gag tgt atc tat gtg gaa ccg     1104
Val Lys Ala Met Trp Arg Glu Ala Lys Glu Cys Ile Tyr Val Glu Pro
        355                 360                 365 gac agg caa ggt gag aag aaa ggt gtg ttc tgg tac aac aat aag tta t   1153
Asp Arg Gln Gly Glu Lys Lys Gly Val Phe Trp Tyr Asn Asn Lys Leu
    370                 375                 380 ga                                                                  1155

<210> SEQ ID NO 6
<211> LENGTH: 384
<212> TYPE: PRT
```

<213> ORGANISM: Brassica napus

<400> SEQUENCE: 6

```
Met Gly Ala Gly Gly Arg Met Gln Val Ser Pro Ser Lys Lys Ser
 1               5                  10                  15
Glu Thr Asp Thr Ile Lys Arg Val Pro Cys Glu Thr Pro Phe Thr
                 20                  25                  30
Val Gly Glu Leu Lys Lys Ala Ile Pro Pro His Cys Phe Lys Arg Ser
             35                  40                  45
Ile Pro Arg Ser Phe Ser Tyr Leu Ile Trp Asp Ile Ile Ala Ser
 50                  55                  60
Cys Phe Tyr Tyr Val Ala Thr Thr Tyr Phe Pro Leu Leu Pro His Pro
 65                  70                  75                  80
Leu Ser Tyr Phe Ala Trp Pro Leu Tyr Trp Ala Cys Gln Gly Cys Val
                 85                  90                  95
Leu Thr Gly Val Trp Val Ile Ala His Glu Cys Gly His His Ala Phe
                 100                 105                 110
Ser Asp Tyr Gln Trp Leu Asp Asp Thr Val Gly Leu Ile Phe His Ser
                 115                 120                 125
Phe Leu Leu Val Pro Tyr Phe Ser Trp Lys Tyr Ser His Arg Ser His
 130                 135                 140
His Ser Asn Thr Gly Ser Leu Glu Arg Asp Glu Val Phe Val Pro Lys
 145                 150                 155                 160
Lys Lys Ser Asp Ile Lys Trp Tyr Gly Lys Tyr Leu Asn Asn Pro Leu
                 165                 170                 175
Gly Arg Thr Val Met Leu Thr Val Gln Phe Thr Leu Gly Trp Pro Leu
                 180                 185                 190
Tyr Leu Ala Phe Asn Val Ser Gly Arg Pro Tyr Asp Gly Gly Phe Arg
                 195                 200                 205
Cys His Phe His Pro Asn Ala Pro Ile Tyr Asn Asp Arg Glu Arg Leu
 210                 215                 220
Gln Ile Tyr Ile Ser Asp Ala Gly Ile Leu Ala Val Cys Tyr Gly Leu
 225                 230                 235                 240
Phe Arg Tyr Ala Ala Gly Gln Gly Val Ala Ser Met Val Cys Phe Tyr
                 245                 250                 255
Gly Val Pro Leu Leu Ile Val Asn Gly Phe Leu Val Leu Ile Thr Tyr
                 260                 265                 270
Leu Gln His Thr His Pro Ser Leu Pro His Tyr Asp Ser Ser Glu Trp
                 275                 280                 285
Asp Trp Phe Arg Gly Ala Leu Ala Thr Val Asp Arg Asp Tyr Gly Ile
 290                 295                 300
Leu Asn Lys Val Phe His Asn Ile Thr Asp Thr His Val Ala His His
 305                 310                 315                 320
Pro Phe Ser Thr Met Pro His Tyr His Ala Met Glu Ala Thr Lys Ala
                 325                 330                 335
Ile Lys Pro Ile Leu Gly Glu Tyr Tyr Gln Phe Asp Gly Thr Pro Val
                 340                 345                 350
Val Lys Ala Met Trp Arg Glu Ala Lys Glu Cys Ile Tyr Val Glu Pro
                 355                 360                 365
Asp Arg Gln Gly Glu Lys Lys Gly Val Phe Trp Tyr Asn Asn Lys Leu
 370                 375                 380
```

<210> SEQ ID NO 7
<211> LENGTH: 1155

```
<212> TYPE: DNA
<213> ORGANISM: Brassica npaus
<220> FEATURE:
<221> NAME/KEY: CDS
<222> LOCATION: (1)..(1152)

<400> SEQUENCE: 7
```

| | | | | | | | | | | | | | | | | |
|---|---|---|---|---|---|---|---|---|---|---|---|---|---|---|---|---|
| atg | ggt | gca | ggt | gga | aga | atg | caa | gtg | tct | cct | ccc | tcc | aag | aag | tct | 48 |
| Met | Gly | Ala | Gly | Gly | Arg | Met | Gln | Val | Ser | Pro | Pro | Ser | Lys | Lys | Ser | |
| 1 | | | | 5 | | | | | 10 | | | | | 15 | | |
| gaa | acc | gac | acc | atc | aag | cgc | gta | ccc | tgc | gag | aca | ccg | ccc | ttc | act | 96 |
| Glu | Thr | Asp | Thr | Ile | Lys | Arg | Val | Pro | Cys | Glu | Thr | Pro | Pro | Phe | Thr | |
| | | | 20 | | | | | 25 | | | | | 30 | | | |
| gtc | gga | gaa | ctc | aag | aaa | gca | atc | cca | ccg | cac | tgt | ttc | aaa | cgc | tcg | 144 |
| Val | Gly | Glu | Leu | Lys | Lys | Ala | Ile | Pro | Pro | His | Cys | Phe | Lys | Arg | Ser | |
| | 35 | | | | | 40 | | | | | 45 | | | | | |
| atc | cct | cgc | tct | ttc | tcc | tac | ctc | atc | tgg | gac | atc | atc | ata | gcc | tcc | 192 |
| Ile | Pro | Arg | Ser | Phe | Ser | Tyr | Leu | Ile | Trp | Asp | Ile | Ile | Ile | Ala | Ser | |
| | 50 | | | | | 55 | | | | | 60 | | | | | |
| tgc | ttc | tac | tac | gtc | gcc | acc | act | tac | ttc | cct | ctc | ctc | cct | cac | cct | 240 |
| Cys | Phe | Tyr | Tyr | Val | Ala | Thr | Thr | Tyr | Phe | Pro | Leu | Leu | Pro | His | Pro | |
| 65 | | | | | 70 | | | | | 75 | | | | | 80 | |
| ctc | tcc | tac | ttc | gcc | tgg | cct | ctc | tac | tgg | gcc | tgc | caa | ggg | tgc | gtc | 288 |
| Leu | Ser | Tyr | Phe | Ala | Trp | Pro | Leu | Tyr | Trp | Ala | Cys | Gln | Gly | Cys | Val | |
| | | | | 85 | | | | | 90 | | | | | 95 | | |
| cta | acc | ggc | gtc | tgg | gtc | ata | gcc | cac | gag | tgc | ggc | cac | cac | gcc | ttc | 336 |
| Leu | Thr | Gly | Val | Trp | Val | Ile | Ala | His | Glu | Cys | Gly | His | His | Ala | Phe | |
| | | | 100 | | | | | 105 | | | | | 110 | | | |
| agc | gac | tac | cag | tgg | ctt | gac | gac | acc | gtc | ggt | ctc | atc | ttc | cac | tcc | 384 |
| Ser | Asp | Tyr | Gln | Trp | Leu | Asp | Asp | Thr | Val | Gly | Leu | Ile | Phe | His | Ser | |
| | | 115 | | | | | 120 | | | | | 125 | | | | |
| ttc | ctc | ctc | gtc | cct | tac | ttc | tcc | tgg | aag | tac | agt | cat | cgc | agc | cac | 432 |
| Phe | Leu | Leu | Val | Pro | Tyr | Phe | Ser | Trp | Lys | Tyr | Ser | His | Arg | Ser | His | |
| | 130 | | | | | 135 | | | | | 140 | | | | | |
| cat | tcc | aac | act | ggc | tcc | ctc | gag | aga | gac | gaa | gtg | ttt | gtc | ccc | aag | 480 |
| His | Ser | Asn | Thr | Gly | Ser | Leu | Glu | Arg | Asp | Glu | Val | Phe | Val | Pro | Lys | |
| 145 | | | | | 150 | | | | | 155 | | | | | 160 | |
| aag | aag | tca | gac | atc | aag | tgg | tac | ggc | aag | tac | cac | aac | aac | cct | ttg | 528 |
| Lys | Lys | Ser | Asp | Ile | Lys | Trp | Tyr | Gly | Lys | Tyr | His | Asn | Asn | Pro | Leu | |
| | | | | 165 | | | | | 170 | | | | | 175 | | |
| gga | cgc | acc | gtg | atg | tta | acg | gtt | cag | ttc | act | ctc | ggc | tgg | ccg | ttg | 576 |
| Gly | Arg | Thr | Val | Met | Leu | Thr | Val | Gln | Phe | Thr | Leu | Gly | Trp | Pro | Leu | |
| | | | 180 | | | | | 185 | | | | | 190 | | | |
| tac | tta | gcc | ttc | aac | gtc | tcg | gga | aga | cct | tac | gac | ggc | ggc | ttc | cgt | 624 |
| Tyr | Leu | Ala | Phe | Asn | Val | Ser | Gly | Arg | Pro | Tyr | Asp | Gly | Gly | Phe | Arg | |
| | | 195 | | | | | 200 | | | | | 205 | | | | |
| tgc | cat | ttc | cac | ccc | aac | gct | ccc | atc | tac | aac | gac | cgc | gag | cgt | ctc | 672 |
| Cys | His | Phe | His | Pro | Asn | Ala | Pro | Ile | Tyr | Asn | Asp | Arg | Glu | Arg | Leu | |
| | 210 | | | | | 215 | | | | | 220 | | | | | |
| cag | ata | tac | atc | tcc | gac | gct | ggc | atc | ctc | gcc | gtc | tgc | tac | ggt | ctc | 720 |
| Gln | Ile | Tyr | Ile | Ser | Asp | Ala | Gly | Ile | Leu | Ala | Val | Cys | Tyr | Gly | Leu | |
| 225 | | | | | 230 | | | | | 235 | | | | | 240 | |
| ttc | cgt | tac | gcc | gcc | ggc | cag | gga | gtg | gcc | tcg | atg | gtc | tgc | ttc | tac | 768 |
| Phe | Arg | Tyr | Ala | Ala | Gly | Gln | Gly | Val | Ala | Ser | Met | Val | Cys | Phe | Tyr | |
| | | | | 245 | | | | | 250 | | | | | 255 | | |
| gga | gtc | ccg | ctt | ctg | att | gtc | aat | ggt | ttc | ctc | gtg | ttg | atc | act | tac | 816 |
| Gly | Val | Pro | Leu | Leu | Ile | Val | Asn | Gly | Phe | Leu | Val | Leu | Ile | Thr | Tyr | |
| | | | 260 | | | | | 265 | | | | | 270 | | | |
| ttg | cag | cac | acg | cat | cct | tcc | ctg | cct | cac | tac | gat | tcg | tcc | gag | tgg | 864 |
| Leu | Gln | His | Thr | His | Pro | Ser | Leu | Pro | His | Tyr | Asp | Ser | Ser | Glu | Trp | |
| | | 275 | | | | | 280 | | | | | 285 | | | | |

```
gat tgg ttc agg gga gct ttg gct acc gtt gac aga gac tac gga atc          912
Asp Trp Phe Arg Gly Ala Leu Ala Thr Val Asp Arg Asp Tyr Gly Ile
    290                 295                 300 ttg aac aag gtc ttc cac aat att acc gac acg cac gtg gcc cat cat          960
Leu Asn Lys Val Phe His Asn Ile Thr Asp Thr His Val Ala His His
305                 310                 315                 320 ccg ttc tcc acg atg ccg cat tat cac gcg atg gaa gct acc aag gcg         1008
Pro Phe Ser Thr Met Pro His Tyr His Ala Met Glu Ala Thr Lys Ala
                325                 330                 335 ata aag ccg ata ctg gga gag tat tat cag ttc gat ggg acg ccg gtg         1056
Ile Lys Pro Ile Leu Gly Glu Tyr Tyr Gln Phe Asp Gly Thr Pro Val
            340                 345                 350 gtt aag gcg atg tgg agg gag gcg aag gag tgt atc tat gtg gaa ccg         1104
Val Lys Ala Met Trp Arg Glu Ala Lys Glu Cys Ile Tyr Val Glu Pro
        355                 360                 365 gac agg caa ggt gag aag aaa ggt gtg ttc tgg tac aac aat aag tta t       1153
Asp Arg Gln Gly Glu Lys Lys Gly Val Phe Trp Tyr Asn Asn Lys Leu
    370                 375                 380 ga                                                                      1155

<210> SEQ ID NO 8
<211> LENGTH: 384
<212> TYPE: PRT
<213> ORGANISM: Brassica napus

<400> SEQUENCE: 8

Met Gly Ala Gly Gly Arg Met Gln Val Ser Pro Ser Lys Lys Ser
 1               5                  10                  15

Glu Thr Asp Thr Ile Lys Arg Val Pro Cys Glu Thr Pro Pro Phe Thr
                20                  25                  30

Val Gly Glu Leu Lys Lys Ala Ile Pro Pro His Cys Phe Lys Arg Ser
            35                  40                  45

Ile Pro Arg Ser Phe Ser Tyr Leu Ile Trp Asp Ile Ile Ala Ser
    50                  55                  60

Cys Phe Tyr Tyr Val Ala Thr Thr Tyr Phe Pro Leu Leu Pro His Pro
65                  70                  75                  80

Leu Ser Tyr Phe Ala Trp Pro Leu Tyr Trp Ala Cys Gln Gly Cys Val
                85                  90                  95

Leu Thr Gly Val Trp Val Ile Ala His Glu Cys Gly His His Ala Phe
            100                 105                 110

Ser Asp Tyr Gln Trp Leu Asp Asp Thr Val Gly Leu Ile Phe His Ser
        115                 120                 125

Phe Leu Leu Val Pro Tyr Phe Ser Trp Lys Tyr Ser His Arg Ser His
    130                 135                 140

His Ser Asn Thr Gly Ser Leu Glu Arg Asp Glu Val Phe Val Pro Lys
145                 150                 155                 160

Lys Lys Ser Asp Ile Lys Trp Tyr Gly Lys Tyr His Asn Asn Pro Leu
                165                 170                 175

Gly Arg Thr Val Met Leu Thr Val Gln Phe Thr Leu Gly Trp Pro Leu
            180                 185                 190

Tyr Leu Ala Phe Asn Val Ser Gly Arg Pro Tyr Asp Gly Gly Phe Arg
        195                 200                 205

Cys His Phe His Pro Asn Ala Pro Ile Tyr Asn Asp Arg Glu Arg Leu
    210                 215                 220

Gln Ile Tyr Ile Ser Asp Ala Gly Ile Leu Ala Val Cys Tyr Gly Leu
225                 230                 235                 240
```

-continued

```
Phe Arg Tyr Ala Ala Gly Gln Gly Val Ala Ser Met Val Cys Phe Tyr
            245                 250                 255
Gly Val Pro Leu Leu Ile Val Asn Gly Phe Leu Val Leu Ile Thr Tyr
            260                 265                 270
Leu Gln His Thr His Pro Ser Leu Pro His Tyr Asp Ser Ser Glu Trp
            275                 280                 285
Asp Trp Phe Arg Gly Ala Leu Ala Thr Val Asp Arg Asp Tyr Gly Ile
            290                 295                 300
Leu Asn Lys Val Phe His Asn Ile Thr Asp Thr His Val Ala His His
305                 310                 315                 320
Pro Phe Ser Thr Met Pro His Tyr His Ala Met Glu Ala Thr Lys Ala
            325                 330                 335
Ile Lys Pro Ile Leu Gly Glu Tyr Tyr Gln Phe Asp Gly Thr Pro Val
            340                 345                 350
Val Lys Ala Met Trp Arg Glu Ala Lys Glu Cys Ile Tyr Val Glu Pro
            355                 360                 365
Asp Arg Gln Gly Glu Lys Lys Gly Val Phe Trp Tyr Asn Asn Lys Leu
370                 375                 380
```

<210> SEQ ID NO 9
<211> LENGTH: 23
<212> TYPE: DNA
<213> ORGANISM: Brassica napus

<400> SEQUENCE: 9
catgggtgca ggtggaagaa tgc                                   23

<210> SEQ ID NO 10
<211> LENGTH: 21
<212> TYPE: DNA
<213> ORGANISM: Brassica napus

<400> SEQUENCE: 10
gtttcttctt tgcttcataa c                                     21

<210> SEQ ID NO 11
<211> LENGTH: 23
<212> TYPE: DNA
<213> ORGANISM: Brassica napus

<400> SEQUENCE: 11
catgggtgca ggtggaagaa tgc                                   23

<210> SEQ ID NO 12
<211> LENGTH: 21
<212> TYPE: DNA
<213> ORGANISM: Brassica napus

<400> SEQUENCE: 12
tctttcacca tcatcatatc c                                     21

<210> SEQ ID NO 13
<211> LENGTH: 19
<212> TYPE: DNA
<213> ORGANISM: Brassica napus

<400> SEQUENCE: 13
gtctgggtca tagcccacg                                        19

```
<210> SEQ ID NO 14
<211> LENGTH: 19
<212> TYPE: DNA
<213> ORGANISM: Brassica napus

<400> SEQUENCE: 14
gtctgggtca tagcccaca                                              19

<210> SEQ ID NO 15
<211> LENGTH: 17
<212> TYPE: DNA
<213> ORGANISM: Brassica napus

<400> SEQUENCE: 15
ctgggtcata gcccatg                                                17

<210> SEQ ID NO 16
<211> LENGTH: 17
<212> TYPE: DNA
<213> ORGANISM: Brassica napus

<400> SEQUENCE: 16
ctgggtcata gcccaca                                                17

<210> SEQ ID NO 17
<211> LENGTH: 5
<212> TYPE: PRT
<213> ORGANISM: Artificial Sequence
<220> FEATURE:
<223> OTHER INFORMATION: fragment
<220> FEATURE:
<221> NAME/KEY: Variant
<222> LOCATION: 2
<223> OTHER INFORMATION: Xaa = Asp or Glu
<220> FEATURE:
<221> NAME/KEY: Variant
<222> LOCATION: 4
<223> OTHER INFORMATION: Xaa = Ala or Gly

<400> SEQUENCE: 17

His Xaa Cys Xaa His
 1               5

<210> SEQ ID NO 18
<211> LENGTH: 6
<212> TYPE: PRT
<213> ORGANISM: Artificial Sequence
<220> FEATURE:
<223> OTHER INFORMATION: Consensus sequence

<400> SEQUENCE: 18

Ala Ile Pro Pro His Cys
 1               5

<210> SEQ ID NO 19
<211> LENGTH: 6
<212> TYPE: PRT
<213> ORGANISM: Artificial Sequence
<220> FEATURE:
<223> OTHER INFORMATION: Consensus sequence

<400> SEQUENCE: 19

Ala Ile Pro Lys His Cys
 1               5

<210> SEQ ID NO 20
<211> LENGTH: 6
```

```
<212> TYPE: PRT
<213> ORGANISM: Artificial Sequence
<220> FEATURE:
<223> OTHER INFORMATION: Consensus sequence
<220> FEATURE:
<221> NAME/KEY: VARIANT
<222> LOCATION: 4
<223> OTHER INFORMATION: Xaa = Pro or Lys

<400> SEQUENCE: 20

Ala Ile Pro Xaa His Cys
 1               5

<210> SEQ ID NO 21
<211> LENGTH: 5
<212> TYPE: PRT
<213> ORGANISM: Artificial Sequence
<220> FEATURE:
<223> OTHER INFORMATION: Consensus sequence
<220> FEATURE:
<221> NAME/KEY: VARIANT
<222> LOCATION: 3
<223> OTHER INFORMATION: Xaa = Leu or Ile

<400> SEQUENCE: 21

Trp Pro Xaa Tyr Trp
 1               5

<210> SEQ ID NO 22
<211> LENGTH: 5
<212> TYPE: PRT
<213> ORGANISM: Artificial Sequence
<220> FEATURE:
<223> OTHER INFORMATION: Consensus sequence

<400> SEQUENCE: 22

Trp Pro Leu Tyr Trp
 1               5

<210> SEQ ID NO 23
<211> LENGTH: 6
<212> TYPE: PRT
<213> ORGANISM: Artificial Sequence
<220> FEATURE:
<223> OTHER INFORMATION: Consensus sequence

<400> SEQUENCE: 23

Ala His Glu Cys Gly His
 1               5

<210> SEQ ID NO 24
<211> LENGTH: 6
<212> TYPE: PRT
<213> ORGANISM: Artificial Sequence
<220> FEATURE:
<223> OTHER INFORMATION: Consensus sequence

<400> SEQUENCE: 24

Gly His Asp Cys Gly His
 1               5

<210> SEQ ID NO 25
<211> LENGTH: 6
<212> TYPE: PRT
<213> ORGANISM: Artificial Sequence
<220> FEATURE:
<223> OTHER INFORMATION: Consensus sequence
<220> FEATURE:
<221> NAME/KEY: VARIANT
```

```
<222> LOCATION: 1
<223> OTHER INFORMATION: Xaa = Ala or Gly
<220> FEATURE:
<221> NAME/KEY: VARIANT
<222> LOCATION: 3
<223> OTHER INFORMATION: Xaa = Asp or Glu

<400> SEQUENCE: 25

Xaa His Xaa Cys Gly His
 1               5

<210> SEQ ID NO 26
<211> LENGTH: 5
<212> TYPE: PRT
<213> ORGANISM: Artificial Sequence
<220> FEATURE:
<223> OTHER INFORMATION: Consensus sequence

<400> SEQUENCE: 26

Leu Leu Val Pro Tyr
 1               5

<210> SEQ ID NO 27
<211> LENGTH: 5
<212> TYPE: PRT
<213> ORGANISM: Artificial Sequence
<220> FEATURE:
<223> OTHER INFORMATION: Consensus sequence

<400> SEQUENCE: 27

Ile Leu Val Pro Tyr
 1               5

<210> SEQ ID NO 28
<211> LENGTH: 5
<212> TYPE: PRT
<213> ORGANISM: Artificial Sequence
<220> FEATURE:
<223> OTHER INFORMATION: Consensus sequence
<220> FEATURE:
<221> NAME/KEY: VARIANT
<222> LOCATION: 1
<223> OTHER INFORMATION: Xaa = Leu or Ile

<400> SEQUENCE: 28

Xaa Leu Val Pro Tyr
 1               5

<210> SEQ ID NO 29
<211> LENGTH: 6
<212> TYPE: PRT
<213> ORGANISM: Artificial Sequence
<220> FEATURE:
<223> OTHER INFORMATION: Consensus sequence

<400> SEQUENCE: 29

Trp Lys Tyr Ser His Arg
 1               5

<210> SEQ ID NO 30
<211> LENGTH: 6
<212> TYPE: PRT
<213> ORGANISM: Artificial Sequence
<220> FEATURE:
<223> OTHER INFORMATION: Consensus sequence

<400> SEQUENCE: 30

Trp Arg Ile Ser His Arg
```

<210> SEQ ID NO 31
<211> LENGTH: 6
<212> TYPE: PRT
<213> ORGANISM: Artificial Sequence
<220> FEATURE:
<223> OTHER INFORMATION: Consensus sequence
<220> FEATURE:
<221> NAME/KEY: VARIANT
<222> LOCATION: 2
<223> OTHER INFORMATION: Xaa = Lys or Arg
<220> FEATURE:
<221> NAME/KEY: VARIANT
<222> LOCATION: 3
<223> OTHER INFORMATION: Xaa = Tyr or Ile

<400> SEQUENCE: 31

Trp Xaa Xaa Ser His Arg
 1               5

<210> SEQ ID NO 32
<211> LENGTH: 6
<212> TYPE: PRT
<213> ORGANISM: Artificial Sequence
<220> FEATURE:
<223> OTHER INFORMATION: Consensus sequence

<400> SEQUENCE: 32

Ser His Arg Arg His His
 1               5

<210> SEQ ID NO 33
<211> LENGTH: 6
<212> TYPE: PRT
<213> ORGANISM: Artificial Sequence
<220> FEATURE:
<223> OTHER INFORMATION: Consensus sequence

<400> SEQUENCE: 33

Ser His Arg Thr His His
 1               5

<210> SEQ ID NO 34
<211> LENGTH: 6
<212> TYPE: PRT
<213> ORGANISM: Artificial Sequence
<220> FEATURE:
<223> OTHER INFORMATION: Consensus sequence
<220> FEATURE:
<221> NAME/KEY: VARIANT
<222> LOCATION: 4
<223> OTHER INFORMATION: Xaa = Arg or Thr

<400> SEQUENCE: 34

Ser His Arg Xaa His His
 1               5

<210> SEQ ID NO 35
<211> LENGTH: 5
<212> TYPE: PRT
<213> ORGANISM: Artificial Sequence
<220> FEATURE:
<223> OTHER INFORMATION: Consensus sequence

<400> SEQUENCE: 35

Ile Thr Tyr Leu Gln
 1               5

```
<210> SEQ ID NO 36
<211> LENGTH: 5
<212> TYPE: PRT
<213> ORGANISM: Artificial Sequence
<220> FEATURE:
<223> OTHER INFORMATION: Consensus sequence

<400> SEQUENCE: 36

Val Thr Tyr Leu His
 1               5

<210> SEQ ID NO 37
<211> LENGTH: 5
<212> TYPE: PRT
<213> ORGANISM: Artificial Sequence
<220> FEATURE:
<223> OTHER INFORMATION: Consensus sequence
<220> FEATURE:
<221> NAME/KEY: VARIANT
<222> LOCATION: 1
<223> OTHER INFORMATION: Xaa = Ile or Val
<220> FEATURE:
<221> NAME/KEY: VARIANT
<222> LOCATION: 5
<223> OTHER INFORMATION: Xaa = Gln or His

<400> SEQUENCE: 37

Xaa Thr Tyr Leu Xaa
 1               5

<210> SEQ ID NO 38
<211> LENGTH: 4
<212> TYPE: PRT
<213> ORGANISM: Artificial Sequence
<220> FEATURE:
<223> OTHER INFORMATION: Consensus sequence

<400> SEQUENCE: 38

Leu Pro His Tyr
 1

<210> SEQ ID NO 39
<211> LENGTH: 4
<212> TYPE: PRT
<213> ORGANISM: Artificial Sequence
<220> FEATURE:
<223> OTHER INFORMATION: Consensus sequence

<400> SEQUENCE: 39

Leu Pro Trp Tyr
 1

<210> SEQ ID NO 40
<211> LENGTH: 4
<212> TYPE: PRT
<213> ORGANISM: Artificial Sequence
<220> FEATURE:
<223> OTHER INFORMATION: Consensus sequence
<220> FEATURE:
<221> NAME/KEY: VARIANT
<222> LOCATION: 3
<223> OTHER INFORMATION: Xaa = His or Trp

<400> SEQUENCE: 40

Leu Pro Xaa Tyr
 1

<210> SEQ ID NO 41
```

```
<211> LENGTH: 6
<212> TYPE: PRT
<213> ORGANISM: Artificial Sequence
<220> FEATURE:
<223> OTHER INFORMATION: Consensus sequence
<220> FEATURE:
<221> NAME/KEY: VARIANT
<222> LOCATION: 3
<223> OTHER INFORMATION: Xaa = Arg or Lys

<400> SEQUENCE: 41

Trp Leu Xaa Gly Ala Leu
1               5

<210> SEQ ID NO 42
<211> LENGTH: 6
<212> TYPE: PRT
<213> ORGANISM: Artificial Sequence
<220> FEATURE:
<223> OTHER INFORMATION: Consensus sequence

<400> SEQUENCE: 42

Tyr Leu Arg Gly Gly Leu
1               5

<210> SEQ ID NO 43
<211> LENGTH: 6
<212> TYPE: PRT
<213> ORGANISM: Artificial Sequence
<220> FEATURE:
<223> OTHER INFORMATION: Consensus sequence
<220> FEATURE:
<221> NAME/KEY: VARIANT
<222> LOCATION: 1
<223> OTHER INFORMATION: Xaa = Trp or Tyr
<220> FEATURE:
<221> NAME/KEY: VARIANT
<222> LOCATION: 3
<223> OTHER INFORMATION: Xaa = Arg or Lys
<220> FEATURE:
<221> NAME/KEY: VARIANT
<222> LOCATION: 5
<223> OTHER INFORMATION: Xaa = Ala or Gly

<400> SEQUENCE: 43

Xaa Leu Xaa Gly Xaa Leu
1               5

<210> SEQ ID NO 44
<211> LENGTH: 7
<212> TYPE: PRT
<213> ORGANISM: Artificial Sequence
<220> FEATURE:
<223> OTHER INFORMATION: Consensus sequence

<400> SEQUENCE: 44

Thr Val Asp Arg Asp Tyr Gly
1               5

<210> SEQ ID NO 45
<211> LENGTH: 7
<212> TYPE: PRT
<213> ORGANISM: Artificial Sequence
<220> FEATURE:
<223> OTHER INFORMATION: Consensus sequence

<400> SEQUENCE: 45

Thr Leu Asp Arg Asp Tyr Gly
1               5
```

```
<210> SEQ ID NO 46
<211> LENGTH: 7
<212> TYPE: PRT
<213> ORGANISM: Artificial Sequence
<220> FEATURE:
<223> OTHER INFORMATION: Consensus sequence
<220> FEATURE:
<221> NAME/KEY: VARIANT
<222> LOCATION: 2
<223> OTHER INFORMATION: Xaa = Val or Leu

<400> SEQUENCE: 46

Thr Xaa Asp Arg Asp Tyr Gly
 1               5

<210> SEQ ID NO 47
<211> LENGTH: 8
<212> TYPE: PRT
<213> ORGANISM: Artificial Sequence
<220> FEATURE:
<223> OTHER INFORMATION: Consensus sequence

<400> SEQUENCE: 47

Thr His Val Ala His His Leu Phe
 1               5

<210> SEQ ID NO 48
<211> LENGTH: 8
<212> TYPE: PRT
<213> ORGANISM: Artificial Sequence
<220> FEATURE:
<223> OTHER INFORMATION: Consensus sequence

<400> SEQUENCE: 48

Thr His Val Ile His His Leu Phe
 1               5

<210> SEQ ID NO 49
<211> LENGTH: 8
<212> TYPE: PRT
<213> ORGANISM: Artificial Sequence
<220> FEATURE:
<223> OTHER INFORMATION: Consensus sequence
<220> FEATURE:
<221> NAME/KEY: VARIANT
<222> LOCATION: 4
<223> OTHER INFORMATION: Xaa = Ala or Ile

<400> SEQUENCE: 49

Thr His Val Xaa His His Leu Phe
 1               5

<210> SEQ ID NO 50
<211> LENGTH: 10
<212> TYPE: PRT
<213> ORGANISM: Artificial Sequence
<220> FEATURE:
<223> OTHER INFORMATION: Consensus sequence

<400> SEQUENCE: 50

His His Leu Phe Ser Thr Met Pro His Tyr
 1               5                  10

<210> SEQ ID NO 51
<211> LENGTH: 10
<212> TYPE: PRT
<213> ORGANISM: Artificial Sequence
<220> FEATURE:
```

```
<223> OTHER INFORMATION: Consensus sequence

<400> SEQUENCE: 51

His His Leu Phe Pro Gln Ile Pro His Tyr
 1               5                  10

<210> SEQ ID NO 52
<211> LENGTH: 10
<212> TYPE: PRT
<213> ORGANISM: Artificial Sequence
<220> FEATURE:
<223> OTHER INFORMATION: Consensus sequence
<220> FEATURE:
<221> NAME/KEY: VARIANT
<222> LOCATION: 5
<223> OTHER INFORMATION: Xaa = Ser or Pro
<220> FEATURE:
<221> NAME/KEY: VARIANT
<222> LOCATION: 6
<223> OTHER INFORMATION: Xaa = Thr or Gln
<220> FEATURE:
<221> NAME/KEY: VARIANT
<222> LOCATION: 7
<223> OTHER INFORMATION: Xaa = Ile or Met

<400> SEQUENCE: 52

His His Leu Phe Xaa Xaa Xaa Pro His Tyr
 1               5                  10

<210> SEQ ID NO 53
<211> LENGTH: 5
<212> TYPE: PRT
<213> ORGANISM: Brassica napus
<220> FEATURE:

<400> SEQUENCE: 53

His Glu Cys Gly His
 1               5

<210> SEQ ID NO 54
<211> LENGTH: 5
<212> TYPE: PRT
<213> ORGANISM: Brassica napus
<220> FEATURE:

<400> SEQUENCE: 54

His Asp Cys Ala His
 1               5

<210> SEQ ID NO 55
<211> LENGTH: 5
<212> TYPE: PRT
<213> ORGANISM: Brassica napus

<400> SEQUENCE: 55

His Asp Cys Gly His
 1               5

<210> SEQ ID NO 56
<211> LENGTH: 12
<212> TYPE: DNA
<213> ORGANISM: Artificial Sequence
<220> FEATURE:
<223> OTHER INFORMATION: Primer

<400> SEQUENCE: 56
tggtcttttg gt                                                        12
```

```
<210> SEQ ID NO 57
<211> LENGTH: 10
<212> TYPE: DNA
<213> ORGANISM: Artificial Sequence
<220> FEATURE:
<223> OTHER INFORMATION: Primer

<400> SEQUENCE: 57
gtcgacgagg                                                          10

<210> SEQ ID NO 58
<211> LENGTH: 12
<212> TYPE: DNA
<213> ORGANISM: Artificial Sequence
<220> FEATURE:
<223> OTHER INFORMATION: Primer

<400> SEQUENCE: 58
agatctggta cc                                                       12
```